United States Patent
Yamada et al.

(10) Patent No.: US 6,346,359 B1
(45) Date of Patent: Feb. 12, 2002

(54) PYRROLOPYRIMIDINEONE COMPOUND AND HEAT-SENSITIVE RECORDING MATERIAL USING THE SAME

(75) Inventors: Hisao Yamada; Mitsuyuki Tsurumi; Kazunori Nigorikawa, all of Shizuoka-ken (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/557,871

(22) Filed: Apr. 24, 2000

(30) Foreign Application Priority Data

Apr. 22, 1999 (JP) ............................................ 11-114929

(51) Int. Cl.$^7$ ............................ G03C 1/72; G03F 7/021; C07D 239/70
(52) U.S. Cl. ........................ 430/138; 430/163; 430/179; 430/182; 544/282; 544/287; 544/293
(58) Field of Search ................................ 430/138, 163, 430/179, 182; 544/287, 293, 282

(56) References Cited

U.S. PATENT DOCUMENTS

| | | | | |
|---|---|---|---|---|
| 5,407,777 A | * | 4/1995 | Shimada et al. | ............ 430/138 |
| 5,866,293 A | * | 2/1999 | Nomura et al. | ............ 430/138 |
| 5,925,489 A | * | 7/1999 | Kawabuchi et al. | ........ 430/138 |
| 6,228,553 B1 | * | 5/2001 | Matsushita et al. | ......... 430/179 |

FOREIGN PATENT DOCUMENTS

| | | | | |
|---|---|---|---|---|
| JP | 6-130600 | 5/1994 | ............ | G03C/7/38 |
| JP | 11-157221 | 6/1999 | ............ | B41M/5/30 |

OTHER PUBLICATIONS

Abstract of JP–2000044564 (Feb. 15, 2000).*
Abstract of JP–2000038388 (Feb. 8, 2000).*

* cited by examiner

*Primary Examiner*—John S. Chu
(74) *Attorney, Agent, or Firm*—Sughrue Mion, PLLC

(57) ABSTRACT

Disclosed are a pyrrolopyrimidineone compound represented by the following general formula (1) and a heat-sensitive recording material using the pyrrolopyrimidineone compound as a coupler:

General formula (1)

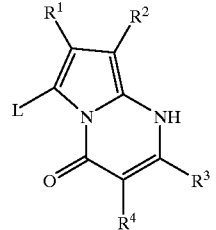

(1)

wherein $R^1$ and $R^2$ each independently represents a hydrogen atom, a halogen atom, an aryl group, an alkyl group, a cyano group, an acyl group, a carbamoyl group, an alkoxycarbonyl group, an aryloxycarbonyl group, an alkylsulfonyl group, or an arylsulfonyl group; $R^3$ represents an amino group, a substituted amino group, a hydroxyl group, an acyloxy group, an arylcarboxyl group, an alkoxy group, an aryloxy group, an alkylthio group, or an arylthio group; $R^4$ represents a hydrogen atom, a halogen atom, or an electron attracting group whose Hammett substituent constant $\sigma_p$ is 0.2 or more; and L represents a substituent group which can leave when the compound reacts with a diazonium salt. The pyrrolopyrimidineone compound produces a good purple to cyan color hue and a sufficient color density.

17 Claims, No Drawings

PYRROLOPYRIMIDINEONE COMPOUND AND HEAT-SENSITIVE RECORDING MATERIAL USING THE SAME

BACKGROUND OF THE INVENTION

1. Field of the Invention

The present invention relates to a novel pyrrolopyrimidineone compound. Further, the present invention relates to a heat-sensitive recording material using a diazonium salt and a coupler as color forming components. More specifically, the present invention relates to a novel purple to cyan color forming type diazo heat-sensitive recording material with excellent color forming property.

2. Related Art

In a color forming reaction system using a coupler and a diazonium salt, color forming reaction rate (coupling rate) often presents a problem. In particular, in a diazo coupling heat-sensitive recording material, it is usually necessary to improve the coupling rate from the standpoint of improving color forming property. Normally, for a particular diazonium salt, the coupling rate is roughly determined by the skeleton of the coupler. The coupling rate can be raised by appropriately changing the substituent group which is at a position other than the coupling position. This change, however, impairs the stability of the coupler and therefore will bring about various defects, such as increase of background coloration due to exposure to light, in a heat-sensitive recording material. That is, coupling activity and coupler stability tend to be incompatible with each other. Accordingly, an effective method, which remarkably increases coupling activity of a coupler skeleton without significant impairment of coupler stability, has not yet been found.

With the increased efficiency of the heat-sensitive material, there has been a strong demand for a heat-sensitive recording material which has sufficient purple to cyan color forming property and also has a long shelf life, improved image storability, and improved image fixation.

A diazonium salt compound is a compound having a very high chemical activity. Because of this chemical activity, the diazonium salt compound easily forms an azo dye by reacting with a coupler which is a phenol derivative, a compound having an active methylene group, or the like. In addition, the diazonium salt compound is photosensitive, and when irradiated with light decomposes and becomes inactive. Because of these properties, a diazonium salt compound has been long utilized as a photo-recording material represented by diazo copy ("Principles of Photographic Science and Engineering-Non-Silver Salt Photographs" edited by the Photographic Society of Japan, 1982, pp.89–117, pp.182–201, published by Corona Publishing Co., Ltd.).

Further, by utilizing the property where a diazonium salt compound is decomposed by light and then becomes inactive, recently the diazonium salt compound is also being used in a recording material requiring the fixation of images. As a typical example of this recording material, there has been proposed a photo-fixation type heat sensitive recording material in which a diazonium salt compound and a coupler are heated in accordance with an image signal so as to form an image by the reaction therebetween, and the image thus formed is then fixed by irradiation with light (for example, H. Sato et al., Journal of the Image Electronics Society of Japan, Vol. 11(1982), No.4, pp.290–296).

However, these recording materials utilizing a diazonium salt compound as a color forming component have been associated with the drawback that the shelf life of the recording material is short. This is because the activity of the diazonium salt compound is so high that the diazonium salt compound undergoes a gradual thermal decomposition even in a dark place and the diazonium salt compound becomes non-reactive. One of the measures to be taken to alleviate this drawback is a method in which the diazonium salt compound is enclosed in microcapsules. Since this method enables the diazonium salt compound to be separated from compounds, such as water or a base, which accelerate the decomposition of the diazonium salt compound, it has become possible to remarkably increase the shelf life of the recording material (T. Usami et al., Journal of the Electrophotographic Society of Japan, Vol. 26(1987), No.2, pp.115–125).

If the microcapsules are composed of a wall, which like a urea resin or a urethane resin, has a glass transition temperature, and if that glass transition temperature is slightly higher than room temperature, the capsule wall is impermeable to materials at room temperature but permeable to materials at a temperature greater than or equal to the glass transition temperature. Therefore, such microcapsules are called heat-responsive microcapsules and are useful in a heat-sensitive recording material. That is, a recording material including a substrate and a heat-sensitive recording layer formed thereon, wherein the heat-sensitive recording layer contains heat-responsive microcapsules enclosing a diazonium salt compound, a coupler, and a base, enables the diazonium salt compound to be kept for a long period of time in a stable state. This recording material also makes it possible to easily form a colored image by heating, and to fix the image by irradiation with light.

As stated above, it has become possible to remarkably improve the stability of the diazonium salt compound by encapsulation.

It has been known that the use of 2-hydroxy-3-naphthoic acid anilide as a coupler results in a particularly excellent color forming material for heat-sensitive recording and that the 2-hydroxy-3-naphthoic acid anilide forms a blue dye when subjected to a coupling reaction with a 4-substituted amino-2-alkoxybenzenediazonium salt compound (Japanese Patent Application Laid-Open (JP-A) No. 2-225,082).

However, if a diazonium compound having $\lambda_{max}$ on a longer wavelength side is used as the diazonium salt, the drawback that the raw stock storability of recording material (resistance to background coloration during storage before copying) is reduced has been observed. Meanwhile, when the above-mentioned 2-hydroxy-3-naphthoic acid anilide is used, fixation by irradiation with light is inhibited and the color formed is shifted to a longer wavelength side(cyan region) in the color hue and further the storability (lightfastness) of colored images is insufficient. That is, the drawbacks associated with the use of a diazonium compound having $\lambda_{max}$ on a shorter wavelength side are observed.

As stated above, a heat-sensitive material, which exhibits sufficient purple to cyan color forming property but little absorption of yellow and which has a long shelf life, and exhibits excellent image storability and image fixation, has yet not been obtained.

SUMMARY OF THE INVENTION

In view of the foregoing, the object of the present invention is to provide a novel purple to cyan color forming diazo type heat-sensitive recording material with a long shelf life, excellent image storability and image fixation and to provide a coupler usable in the heat-sensitive recording material.

After extensive studies on couplers, the present inventors have found that a pyrrolopyrimidineone compound represented by the following general formula (1) is useful as a coupler providing a good purple to cyan color hue and a sufficient coloration density. Further, they have found that the heat-sensitive recording material using the pyrrolopyrimidineone compound and the following diazonium salt compound has improved shelf life, image lightfastness, and image fixation as well as excellent purple to cyan color forming property. Based on these findings, they have achieved the present invention.

The present invention is:

<1> a pyrrolopyrimidineone compound represented by the following general formula (1):

General formula (1)

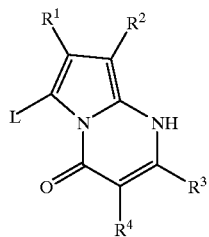

(1)

wherein $R^1$ and $R^2$ each independently represents a hydrogen atom, a halogen atom, an aryl group, an alkyl group, a cyano group, an acyl group, a carbamoyl group, an alkoxycarbonyl group, an aryloxycarbonyl group, an alkylsulfonyl group, or an arylsulfonyl group; $R^3$ represents an amino group, a substituted amino group, a hydroxyl group, an acyloxy group, an arylcarboxyl group, an alkoxy group, an aryloxy group, an alkylthio group, or an arylthio group; $R^4$ represents a hydrogen atom, a halogen atom, or an electron attracting group whose Hammett substituent constant $\sigma_p$ is 0.2 or more and L represents a substituent group which can leave when the compound reacts a reaction with a diazonium salt.

<2> a heat-sensitive recording material comprising a substrate having thereon a heat-sensitive recording layer containing a diazonium salt and a coupler capable of forming a color by reacting with the diazonium salt when heated, wherein the coupler is a pyrrolopyrimidineone compound represented by the following general formula (1):

General formula (1)

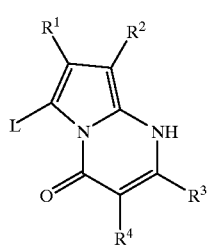

(1)

wherein $R^1$ and $R^2$ each independently represents a hydrogen atom, a halogen atom, an aryl group, an alkyl group, a cyano group, an acyl group, a carbamoyl group, an alkoxycarbonyl group, an aryloxycarbonyl group, an alkylsulfonyl group, or an arylsulfonyl group; $R^3$ represents an amino group, a substituted amino group, a hydroxyl group, an acyloxy group, an arylcarboxyl group, an alkoxy group, an aryloxy group, an alkylthio group, or an arylthio group; $R^4$ represents a hydrogen atom, a halogen atom, or an electron attracting group whose Hammett substituent constant $\sigma_p$ is 0.2 or more; and L represents a substituent group which can leave when the compound undergoes a substitution reaction with a diazonium salt.

DETAILED DESCRIPTION OF PREFERRED EMBODIMENT

The details of the present invention are given below.

The pyrrolopyrimidineone compound of the present invention is characterized in that, when coupled as a coupler with a diazonium salt, the pyrrolopyrimidineone compound provides a good purple to cyan color hue and a sufficient coloration density and increases shelf life, and improves image lightfastness, and image fixation of the heat-sensitive material.

More specifically, the pyrrolopyrimidineone compound of the present invention is a novel compound represented by the general formula (1).

General Formula (1)

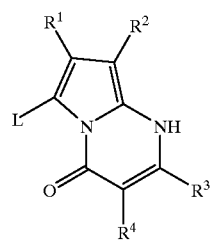

(1)

In the general formula (1), $R^1$ and $R^2$ each independently represents a hydrogen atom, a halogen atom, an aryl group, an alkyl group, a cyano group, an acyl group, a carbamoyl group, an alkoxycarbonyl group, an aryloxycarbonyl group, an alkylsulfonyl group, or an arylsulfonyl group. $R^3$ represents an amino group, a substituted amino group, a hydroxyl group, an acyloxy group, an arylcarboxyl group, an alkoxy group, an aryloxy group, an alkylthio group, or an arylthio group. $R^4$ represents a hydrogen atom, a halogen atom, or an electron attracting group whose Hammett substituent constant $\sigma_p$ is 0.2 or more. L represents a substituent group which can leave when the compound reacts with a diazonium salt.

It is preferable that at least one of $R^1$ and $R^2$ is an electron attracting group whose Hammett substituent constant $\sigma_p$ is 0.2 or more. More preferably at least one of $R^1$ and $R^2$ is an electron attracting group whose Hammett substituent constant $\sigma_p$ is 0.35 or more.

Among the electron attracting groups each having a Hammett substituent constant $\sigma_p$ of 0.20 or more, preferable examples of the groups include, but are not limited to, a cyano group (constant $\sigma_p$ is 0.66), a perfluoroalkyl group (e.g., trifluoromethyl group whose constant $\sigma_p$ is 0.54), an acyl group (e.g., acetyl group whose constant $\sigma_p$ is 0.50 and a benzoyl group (constant $\sigma_p$ is 0.43), a carbamoyl group (constant $\sigma_p$ is 0.36), an alkoxycarbonyl group (e.g., ethoxycarbonyl group whose constant $\sigma_p$ is 0.45), and so on.

Examples of the halogen atom include a fluorine atom, a chlorine atom, a bromine atom, and so on. Among these halogen atoms, a fluorine atom and a chlorine atom are preferable.

Preferable examples of the electron attracting group represented by $R^4$ whose Hammett substituent constant $\sigma_p$ is 0.20 or more include, but are not limited to, an aryl group, a cyano group, an acyl group, a carbamoyl group, an alkoxycarbonyl group, an aryloxycarbonyl group, an alkylsulfonyl group, an arylsulfonyl group, an alkylphosphoryl group, an arylphosphoryl group, a perfluoroalkyl group, and so on.

Among the substituent groups as $R^1$, $R^2$ and $R^4$, the aryl group may be further substituted by an alkyl group, an alkoxy group, an aryloxy group, a halogen atom, a nitro group, a cyano group, a substituted carbamoyl group, a substituted sulfamoyl group, a substituted amino group, a substituted oxycarbamoyl group, a substituted oxysulfonyl group, an alkylthio group, an arylthio group, an alkylsulfonyl group, an arylsulfonyl group, an aryl group, a hydroxyl group, an acyl group, an acyloxy group, a substituted sulfonyloxy group, a substituted aminocarbonyloxy group, a substituted phosphoryloxy group, and the like.

When $R^1$ and $R^2$ each represents an aryl group, the aryl group is an aryl group having 6 to 30 carbon atoms. Examples of the aryl group include a phenyl group, a 2-methylphenyl group, a 2-chlorophenyl group, a 2-methoxyphenyl group, a 2-ethoxyphenyl group, a 2-propoxyphenyl group, a 2-isopropoxyphenyl group, a 2-butoxyphenyl group, a 2-(2-ethylhexyloxy)phenyl group, a 2-octyloxyphenyl group, a 2-undecyloxyphenyl group, a 2-trifluoromethylphenyl group, a 2-(2-ethylhexyloxy)-5-chlorophenyl group, a 2-(2-ethylhexyloxy)-3,5-dichlorophenyl group, a 3-(2,4-di-t-pentylphenoxyethoxy)phenyl group, a 2-(dibutylaminocarbonylethoxy)phenyl group, a 2,4-dichlorophenyl group, a 2,5-dichlorophenyl group, a 2,4,6-trimethylphenyl group, a 3-chlorophenyl group, a 3-nitrophenyl group, a 3-cyanophenyl group, 3-trifluoromethylphenyl group, 3-methoxyphenyl group, a 3-ethoxyphenyl group, a 3-butoxyphenyl group, a 3-(2-ethylhexyloxy)phenyl group, a 3,4-dichlorophenyl group, a 3,5-dichlorophenyl group, a 3,4-dimethoxyphenyl group, a 3,5-dibutoxyphenyl group, a 3-octyloxyphenyl group, a 3-(dibutylaminocarbonylmethoxy)phenyl group, a 3-(di-2-ethylhexylaminocarbonylmethoxy)phenyl group, a 3-dodecyloxyphenyl group, a 4-chlorophenyl group, a 4-cyanophenyl group, a 4-nitrophenyl group, a 4-trifluoromethylphenyl group, 4-methoxyphenyl group, a 4-ethoxyphenyl group, a 4-isopropoxyphenyl group, a 4-butoxyphenyl group, a 4-(2-ethylhexyloxy)phenyl group, a 4-isopentyloxyphenyl group, a 4-(octadecyloxy)phenyl group, a 4-benzylphenyl group, a 4-aminosulfonylphenyl group, a 4-N,N-dibutylaminosulfonylphenyl group, a 4-ethoxycarbonylphenyl group, a 4-(2-ethylhexyloxycarbonyl) phenyl group, a 4-t-octylphenyl group, a 4-fluorophenyl group, a 3-acetylphenyl group, a 2-acetylaminophenyl group, a 2,4-di-t-pentylphenyl group, a 4-(2-ethylhexyloxy)carbonylphenyl group, a 4-methylthiophenyl group, and a 4-(4-chlorophenylthio)phenyl group, a hydroxyphenyl group, a phenylsulfonylphenyl group, a phenylsulfonyloxyphenyl group, a phenylcarbonyloxyphenyl group, a dimethylaminocarbonyloxyphenyl group, a butylcarbonyloxyphenyl group, and so on.

When $R^4$ represents an aryl group, the aryl group is an aryl group having 6 to 30 carbon atoms. Examples of the aryl group include a 3-nitrophenyl group, a 4-nitrophenyl group, a 4-cyanophenyl group, a 4-trifluoromethylphenyl group, a 4-methylsulfonylphenyl group, a 4-ethylsulfonylphenyl group, a 4-octylsulfonylphenyl group, a 4-phenylsulfonylphenyl group, a pentafluorophenyl group, a pentachlorophenyl group, and so on.

Among the substituent groups represented by $R^1$ and $R^2$, the alkyl group maybe a straight-chain or branched alkyl group and may have an unsaturated bond. The alkyl group may be substituted by an alkoxy group, an aryloxy group, an alkoxycarbonyl group, an aryloxycarbonyl group, an aryl group, a hydroxyl group, a halogen atom, or the like. The aryl group may be further substituted by an alkyl group, an alkoxy group, a nitro group, a cyano group, a hydroxyl group, or a halogen atom.

When $R^1$ and $R^2$ each represents an alkyl group, the alkyl group is an alkyl group having 1 to 30 carbon atoms. Examples of the alkyl group include a methyl group, a trifluoromethyl group, an ethyl group, a butyl group, a hexyl group, an octyl group, a 2-ethylhexyl group, a decyl group, a dodecyl group, an octadecyl group, a propyl group, an isopropyl group, an isobutyl group, a sec-butyl group, a t-butyl group, a pentyl group, a 1-ethylpentyl group, a cyclopentyl group, a cyclohexyl group, an isopentyl group, a heptyl group, a nonyl group, a undecyl group, apropenyl group, a heptadecenyl group, a t-octyl group, an ethoxycarbonylmethyl group, a butoxycarbonylmethyl group, a 2-ethylhexyloxycarbonylmethyl group, a 1-(ethoxycarbonyl)ethyl group, a 2',4'-diisopentylphenyloxymethyl group, a 2',4'-di-t-butylphenyloxymethyl group, an ethoxycarbonylethyl group, a 2-ethylhexyloxycarbonylethyl group, a butyldecyloxycarbonylethyl group, a dibutylaminocarbonylmethyl group, a dibenzylaminocarbonylethyl group, an ethyloxycarbonylpropyl group, a 2-ethylhexyloxycarbonylpropyl group, a 2,4-di-t-amylphenyloxypropyl group, a 1-(2',4'-di-t-amylphenyloxy)propyl group, a 2,4-di-t-butylphenyloxypropyl group, an acetylaminoethyl group, an N,N-dihexylaminocarbonylethyl group, a 2,4-di-t-amyloxyethyloxycarbonylpropyl group, an isostearyloxycarbonylpropyl group, a 1-(2,4-di-t-pentylphenyloxy)propyl group, a 2,4-di-t-pentylphenyloxyethyloxycarbonylpropyl group, a naphthyloxyethyloxycarbonylethyl group, an N-methyl-N-phenylethyloxycarbonylethyl group, a methanesulfonylaminopropyl group, and so on.

Among the substituent groups represented by $R^1$, $R^2$ and $R^4$, the acyl group is preferably an acyl group having 2 to 20 carbon atoms. Examples of the acyl group include an acetyl group, a propanoyl group, a butanoyl group, a hexanoyl group, an octanoyl group, a 2-ethylhexanoyl group, a decanoyl group, a dodecanoyl group, an octadecanoyl group, a 2-cyanopropanoyl group, 1,1-dimethylpropanoyl group, a benzoyl group, a 2-(2,4-di-t-pentylphenyloxy) butanoyl group, a phenoxyacetyl group, and so on.

Among the substituent groups represented by $R^1$, $R^2$ and $R^4$, the carbamoyl group means a substituted or unsubstituted carbamoyl group. Examples of the carbamoyl group include a carbamoyl group, an N-alkylcarbamoyl group, an N-arylcarbamoyl group, an N-acylcarbamoyl group, an N-alkoxycarbonylcarbamoyl group, an N-aryloxycarbonylcarbamoyl group, an N-alkylsulfonylcarbamoyl group, an N-arylsuofonylcarbamoyl group, an N,N-dialkylcarbamoyl group, an N,N-diarylcarbamoyl group, an N-alkyl-N-arylcarbamoyl group, and so on.

The substituted carbamoyl group is preferably a substituted carbamoyl group having 1 to 30 carbon atoms. Examples of the carbamoyl group include an N-methylcarbamoyl group, an N-ethylcarbamoylgroup, an N-propylcarbamoyl group, an N-butylcarbamoyl group, an N-hexylcarbamoyl group, an N-cyclohexylcarbamoyl group, an N-octylcarbamoyl group, an N-2-ethylhexylcarbamoyl group, an N-decylcarbamoyl group, an N-octadecylcarbamoyl group, an N-phenylcarbamoyl group, an N-2-methylphenylcarbamoyl group, an N-2- chlorophenylcarbamoyl group, an N-2-methoxyphenylcarbamoyl group, an N-2-isopropoxyphenylcarbamoyl group, an N-2-(2-ethylhexyloxy)phenylcarbamoyl group, an N-3-chlorophenylcarbamoyl group, an N-3-nitrophenylcarbamoyl group, an N-3-cyanophenylcarbamoyl group, an N-4-methoxyphenycarbamoyl group, an N-4-( 2-ethylhexyloxy)phenylcarbamoyl group, an N-4-cyanophenylcarbamoyl group, an N-acetylcarbamoyl group, an N-benzoylcarbamoyl group, an N-methoxycarbonylcarbamoyl group, an N-ethoxycarbonylcarbamoyl group, an N-butoxycarbonylcarbamoyl group, an N-phenoxycarbonylcarbamoyl group, an N-methylsulfonylcarbamoyl group, an N-ethylsulfonylcarbamoyl group, an N-isopropylsulfonylcarbamoyl group, an N-butylsulfonylcarbamoyl group, an N-octylsulfonylcarbamoyl group, an N-phenylsulfonylcarbamoyl group, an N-(4-methylphenyl)sulfonylcarbamoyl group, an N-(4-chlorophenyl)sulfonylcarbamoyl group, an N-(4-methoxyphenyl)sulfonylcarbamoyl group, an N-[4-(2-ethylhexyloxy)phenyl]sulfonylcarbamoyl group, an N,N-dimethylcarbamoyl group, an N,N-dibutylcarbamoyl group, an N,N-diphenylcarbamoyl group, an N-methyl-N-phenylcarbamoyl group, and so on.

Among the substituent groups represented by $R^1$, $R^2$ and $R^4$, the alkoxycarbonyl group is preferably an alkoxycarbonyl group having 2 to 20 carbon atoms. Examples of the alkoxycarbonyl group include a methoxycarbonyl group, an ethoxycarbonyl group, a propoxycarbonyl group, a butoxycarbonyl group, a hexyloxycarbonyl group, a 2-ethylhexyloxycarbonyl group, an octyloxycarbonyl group, a decyloxycarbonyl group, an octadecyloxycarbonyl group, a phenyloxyethyloxycarbonyl group, a phenyloxypropyloxycarbonyl group, a 2,4-di-t-amylphenyloxyethylcarbonyl group, a 2,6-di-t-butyl-4-methylcyclohexyloxycarbonyl group, an isostearyloxycarbonyl group, and so on.

Among the substituent groups represented by $R^1$, $R^2$ and $R^4$, the aryloxycarbonyl group is preferably an aryloxycarbonyl group having 7 to 30 carbon atoms. Examples of the aryloxycarbonyl group include a 2-methylphenyloxycarbonyl group, a 2-chlorophenyloxycarbonyl group, a 2,6-dimethylphenyloxycarbonyl group, a 2,4,6-trimethylphenyloxycarbonyl group, a 2-methoxyphenyloxycarbonyl group, a 2-butoxyphenyloxycarbonyl group, a 3-cyanophenyloxycarbonyl group, a 3-nitrophenyloxycarbonyl group, a 2,2-ethylhexylphenyloxycarbonyl group, a 3-(2-ethylhexyloxy)phenyloxycarbonyl group, a 4-fluorophenyloxycarbonyl group, a 4-chlorophenyloxycarbonyl group, a 4-cyanophenyloxycarbonyl group, a 4-butoxyphenyloxycarbonyl group, and so on.

Among the substituent groups represented by $R^1$, $R^2$ and $R^4$, the alkysulfonyl group is preferably an alkylsulfonyl group having 1 to 20 carbon atoms. Examples of the alkylsulfonyl group include a methylsulfonyl group, an ethylsulfonyl group, a propylsulfonyl group, an isopropylsulfonyl group, a butylsulfonyl group, a hexylsulfonyl group, a cyclohexylsulfonyl group, an octylsulfonyl group, a 2-ethylhexylsulfonyl group, a decanoylsulfonyl group, a dodecanoylsulfonyl group, an octadecanoylsulfonyl group, a cyanomethylsulfonyl group, and so on.

Among the substituent groups represented by $R^1$, $R^2$ and $R^4$, the arylsulfonyl group is preferably an arylsulfonyl group having 6 to 30 carbon atoms. Examples of the arylsulfonyl group include a phenylsulfonyl group, a 1-naphthylsulfonyl group, a 2-naphthylsulfonyl group, a 2-chlorophenylsulfonyl group, a 2-methylphenylsulfonyl group, a 2-methoxyphenylsulfonyl group, a 2-butoxyphenylsulfonyl group, a 3-chlorophenylsulfonyl group, a 3-trifluoromethylphenylsulfonyl group, a 3-cyanophenylsulfonyl group, a 3-(2-ethylhexyloxy)phenylsulfonyl group, a 3-nitrophenylsulfonyl group, a 4-fluorophenylsulfonyl group, a 4-chlorophenylsulfonyl group, a 4-methylphenylsulfonyl group, a 4-cyanophenylsulfonyl group, a 4-butoxyphenylsulfonyl group, a 4-(2-ethylhexyloxy)phenylsulfonyl group, a 4-octadecylphenylsulfonyl group, and so on.

Among the substituent groups represented by $R^4$, the alkyphosphoryl group is preferably an alkylphosphoryl group having 2 to 40 carbon atoms. Examples of the alkylphosphoryl group include a methylphosphoryl group, an ethylphosphoryl group, a propylphosphoryl group, an isopropylphosphoryl group, a butylphosphoryl group, an isobutylphosphoryl group, a sec-butylphosphoryl group, a t-butylphophoryl group, a pentylphosphoryl group, an iso-pentylphosphoryl group, a hexylphosphoryl group, a heptylphosphoryl group, an octylphosphoryl group, a 2-ethylhexylphosphoryl group, a decylphosphoryl group, a dodecylphosphoryl group, an octadecylphosphoryl group, an ethoxycarbonylmethylphosphoryl group, 2-ethylhexyloxycarbonylmethylphosphoryl group, an aminocarbonylmethylphosphoryl group, an N,N-dibutylaminocarbonylmethylphosphoryl group, an N-methylaminocarbonylmethylphosphoryl group, an N-ethylaminocarbonylmethylphosphoryl group, an N-octylaminocarbonylmethylphosphoryl group, a benzylphosphoryl group, and so on.

Among the substituent groups represented by $R^4$, the arylphosphoryl group is preferably an arylphosphoryl group having 12 to 50 carbon atoms. Examples of the arylphosphoryl group include a phenylphosphoryl group, a 1-naphthylphosphoryl group, a 2-naphthylphosphoryl group, a 2-chlorophenphosphoryl group, a 2-methylphenylphosphoryl group, a 2-methoxyphenylphosphoryl group, a 2-butoxyphenylphosphoryl group, 3-chlorophenylphosphoryl group, a 3-trifluoromethylphenylphosphoryl group, a 3-cyanophenylphosphoryl group, a 3-(2-ethylhexyloxy)phenylphosphoryl group, a 3-nitrophenylphosphoryl group, a 4-fluorophenylphosphoryl group, a 4-cyanophenylphosphoryl group, a 4-butoxyphenylphosphoryl group, a 4-(2-ethylhexyloxy)phenylphosphoryl group, a 4-octadecylphenylphosphoryl group, and so on.

Among the substituent groups represented by $R^4$, the perfluoroalkyl group is preferably a perfluoroalkyl group having 1 to 20 carbon atoms. Examples of the perfluoroalkyl group include a trifluoromethyl group, a pentafluoroethyl group, a heptafluoropropyl group, a nonafluorobutyl group, and so on.

As the substituent group $R^1$, an alkyl group or an aryl group is preferable and an aryl group is the more preferable of these substituent groups.

As the substituent group $R^2$, a cyano group or an alkoxycarbonyl group is preferable and an alkoxycarbonyl group is more preferable.

As the substituent group $R^4$, a carbamoyl group is preferable and an N-arylsulfonylcarbamoyl group is more preferable Among the substituent groups represented by $R^3$, the substituted amino group is preferably a substituted amino group having 1 to 30 carbon atoms. Example of the substituted amino group include an isopropylamino group, an isobutylamino group, a n-hexylamino group, a 2-ethylhexylamino group, an n-octylamino group, an n-decylamino group, an acylamino group, an ethanoylamino group, a propanoylamino group, a butanoylamino group, a hexanoylamino group, a 2-ethylhexanoylamino group, an n-octanoylamino group, an n-decanoylamino group, an n-dodecanoylamino group, a methanesulfonylamino group, an ethanesulfonylamino group, a propanesulfonylamino group, a butanesulfonylamino group, a hexanesulfonylamino group, a 2-ethylhexanesulfonylamino group, an n-octanesulfonylamino group, an n-decanesulfonylamino group, an n-dodecanesulfonylamino group, and so on.

Among the substituent groups represented by $R^3$, the acyloxy group is preferably an acyloxy group having 1 to 20 carbon atoms. Example of the acyloxy group include an acetyloxy group, an isobutanoyloxy group, an n-hexanoyloxy group, a 2-ethylhexanoyloxy group, an n-octanoyloxy group, an n-decanoyloxy group, and so on.

Among the substituent groups represented by $R^3$, the arylcarboxyl group is preferably an arylcarboxyl group having 7 to 30 carbon atoms. Examples of the arylcarboxyl group include a benzoyl group, a 4-methylphenylcarboxyl group, a 4-methoxyphenylcarboxyl group, a 4-chlorophenylcarboxyl group, and so on.

Among the substituent groups represented by $R^3$, the alkoxy group is preferably an alkoxy group having 1 to 20 carbon atoms. Examples of the alkoxy group include a methoxy group, an ethoxy group, a propyloxy group, an isopropyloxy group, an isobutyloxy group, an n-hexyloxy group, a 2-ethylhexyloxy group, an n-octyloxyl group, an n-decyloxy group, an n-dodecyloxy group, and so on.

Among the substituent groups represented by $R^3$, the aryloxy group is preferably an aryloxy group having 7 to 30 carbon atoms. Examples of the aryloxy group include a phenoxy group, a 4-methylphenoxy group, a 4-methoxyphenoxy group, a 4-chlorophenoxy group, and so on.

Among the substituent groups represented by $R^3$, the alkylthio group is preferably an alkylthio group having 1 to 20 carbon atoms. Examples of the alkylthio group include a methylthio group, an ethylthio group, a propylthio group, an isopropylthio group, an isobutylthio group, an n-hexylthio group, a 2-ethylhexylthio group, an n-octylthio group, an n-decylthio group, an n-dodecylthio group, and so on.

Among the substituent groups represented by $R^3$, the arylthio group is preferably an arylthio group having 7 to 30 carbon atoms. Examples of the arylthio group include a phenylthio group, a 4-methylphenylthio group, a 4-methoxyphenylthio group, a 4-chlorophenylthio group, and so on.

The leaving group represented by L is a halogen atom, an aromatic azo group, an alkyl group, an aryl or heterocyclic group, an alkyl or arylsulfonyl group, an arylsulfinyl group, an alkyl or aryl or heterocyclocarbonyl group, binding with the coupling site via an oxygen, nitrogen, sulfur or carbon atom, or a heterocyclic group binding with the coupling site via a nitrogen atom. Examples of the leaving group include a halogen atom, an alkoxy group, an aryloxy group, an acyloxy group, an alkyl or arylsulfonyloxy group, an acylamino group, an alkyl or arylsulfonamide group, an alkoxycarbonyloxy group, an aryloxycarbonyloxy group, an alkyl or aryl or heterocyclothio group, a carbamoylamino group, an arylsulfinyl group, an arylsulfonyl group, a 5- or 6-membered nitrogen-containing heterocyclic group, an imido group, an arylazo group, and so on. The alkyl or heterocyclic group contained in the leaving group may be further substituted by a substituent group such as an alkoxy group, an aryloxy group, a halogen atom, an alkoxylcarbonyl group, an alkylcarbonyloxy group, or the like. If two or more of these substituent groups are present, the substituent groups may be the same or different, and these substituent groups may further have substituent groups.

More specific examples of the leaving group include a halogen atom (e.g., fluorine, bromine, chlorine, and iodine atoms), an alkoxy group (e.g., ethoxy, dodecyloxy, methoxyethycarbamoylmethoxy, carboxypropyloxy, methylsulfonylethoxy, and ethoxycarbonylmethoxy groups), an aryloxy group (e.g., 4-methylphenoxy, 4-chlorophenoxy, 4-methoxyphenoxy, 4-carboxyphenoxy, 3-ethoxycarboxyphenoxy, 3-acetylaminophenoxy, and 2-carboxyphenoxy groups), an acyloxy group (e.g., acetoxy, tetradecanoylxoy, and benzoyloxy groups), an alkyl or arylsulfonyloxy group (e.g., methanesulfonyloxy and toluenesulfonyloxy groups), an acylamino group (e.g., dichloroacetylamino and heptafluorobutylylamino groups), an alkyl or arylsulfonamide group (e.g., methanesulfonamide, trifluoromethanesulfonamide, and p-toluenesulfonamide groups), an alkoxycarbonyloxy group (e.g., ethoxycarbonyloxy and benzyloxycarbonyloxy groups), an aryloxycarbonyloxy group (e.g., phenoxycarbonyloxy group), an alkyl or aryl or heterocyclothio group (e.g., ethylthio, 2-carboxyethylthio, dodecylthio, 1-carboxydodecylthio, phenylthio, 2-butoxy-t-octylphenylthio, and tetrazolylthio groups), an arylsulfonyl group (e.g., 2-butoxy-t-octylphenylsulfonyl group), an arylsulfinyl group (e.g., 2-butoxy-t-octylphenylsulfinyl group), a carbamoylamino group (e.g., N-methylcarbamoylamino and N-phenylcarbamoylamino groups), a 5- or 6-membered nitrogen-containing heterocyclic group (e.g., imidazolyl, pyrazolyl, triazolyl, tetrazolyl, and 1,2-dihydro-2-oxo-1-pyridyl groups), an imido group (e.g., succinimido and hydantoinyl groups), and an arylazo group (e.g., phenyl azo, 4-methoxyphenyl azo groups). These groups may be further substituted.

Typical specific examples of the pyrrolopyrimidineone compounds represented by the general formula (1) of the present invention are given below. However, it should be noted that the present invention is not limited to these compounds.

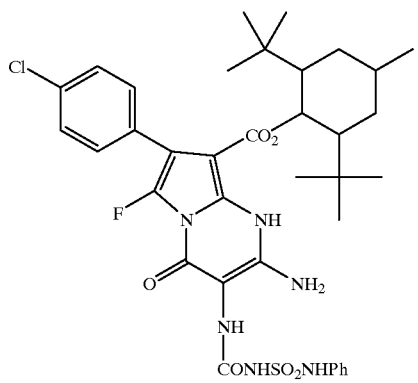

(C-1)

-continued
(C-2)
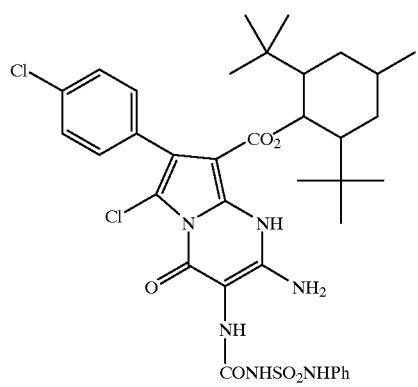
(C-3)
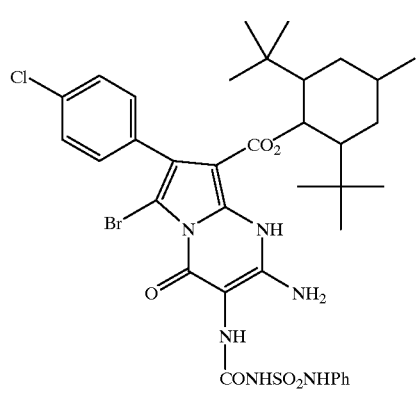
(C-4)
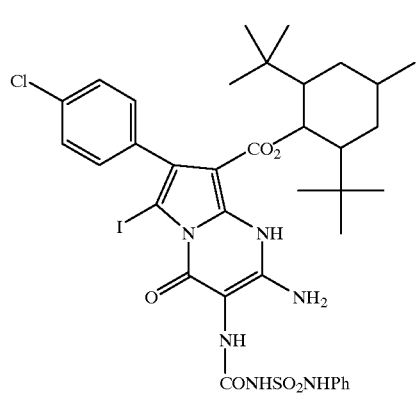
(C-5)
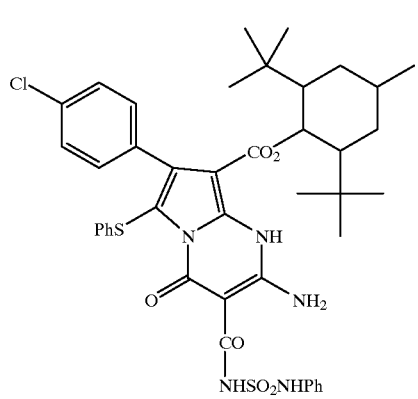
(C-6)
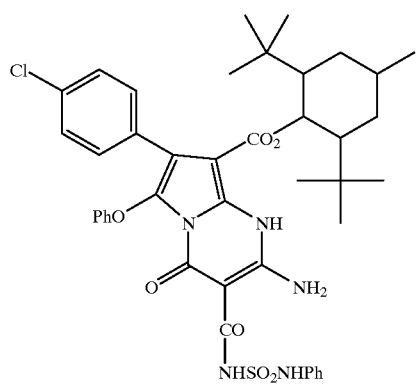
(C-7)
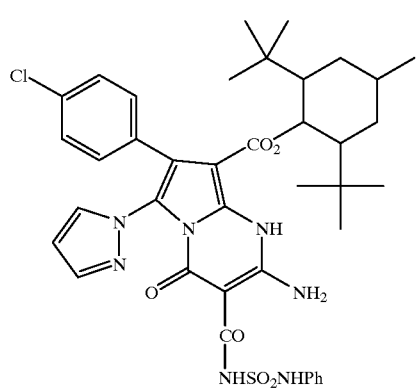
(C-8)
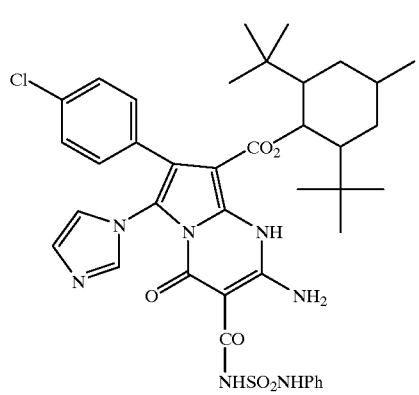
(C-9)
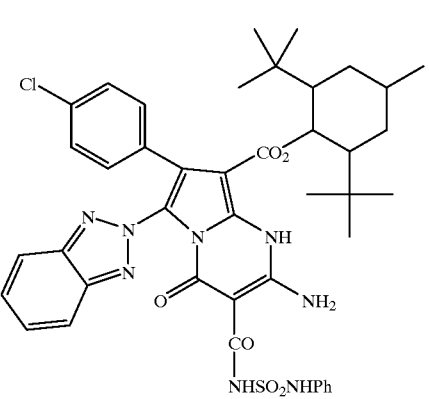

-continued
(C-10)
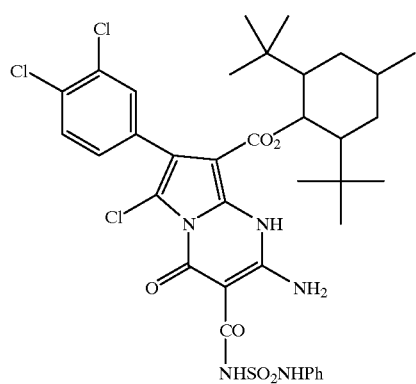
(C-11)
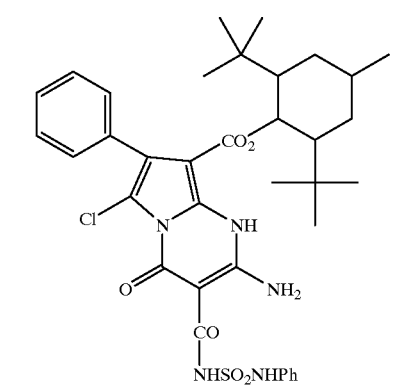
(C-12)
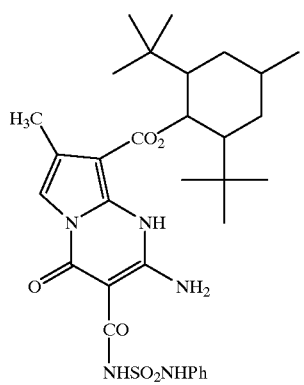
(C-13)
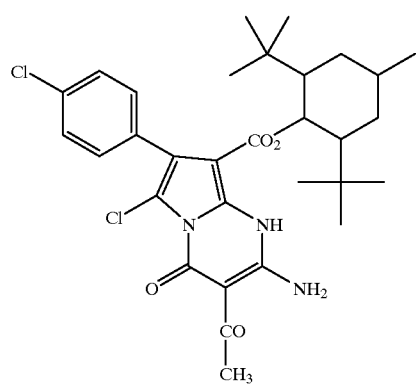
-continued
(C-14)
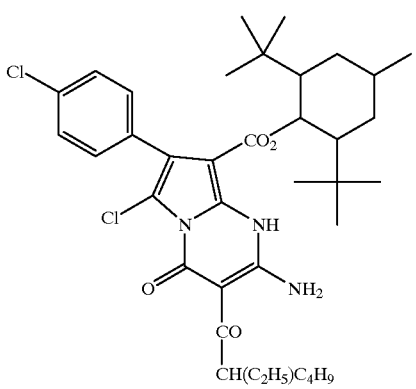
(C-15)
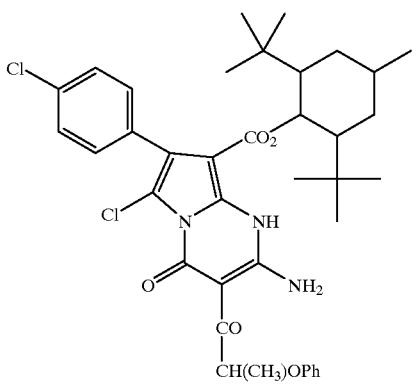
(C-16)
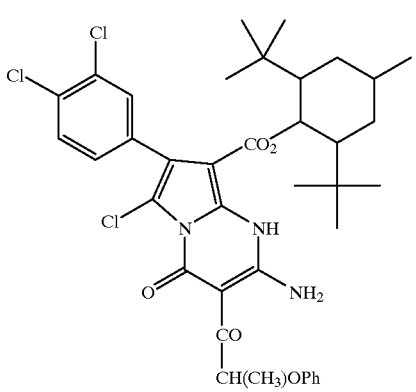
(C-17)
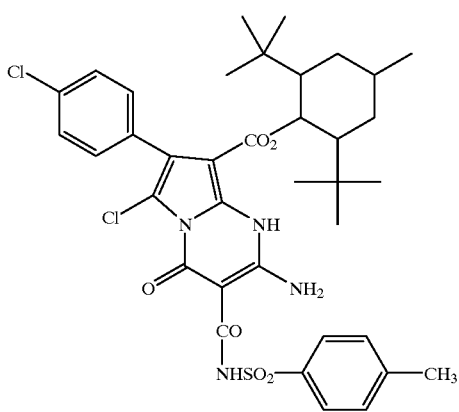

-continued
(C-18)
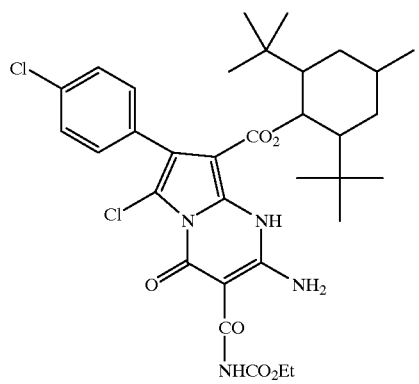
(C-19)
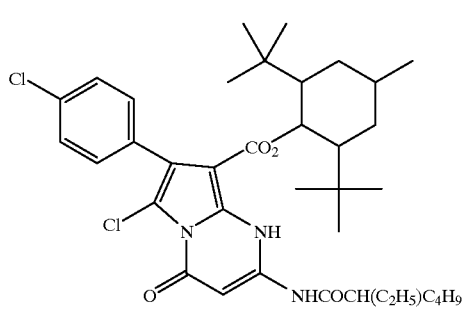
(C-20)
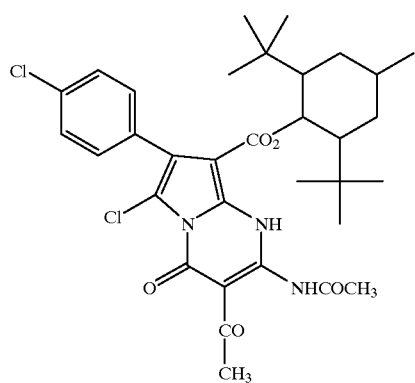
(C-21)
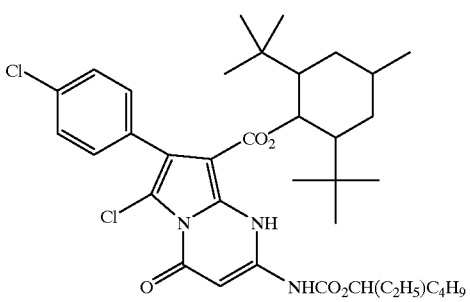
-continued
(C-22)
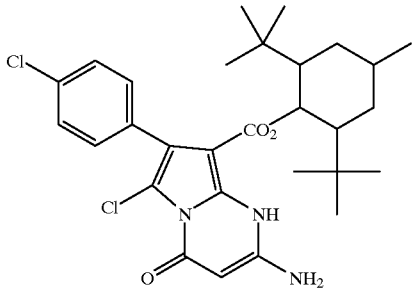
(C-23)
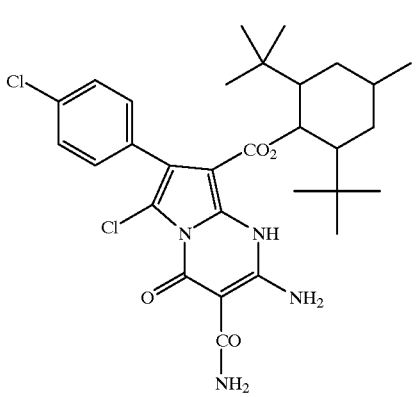
(C-24)
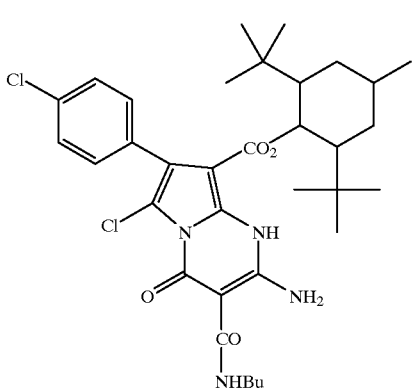
(C-25)
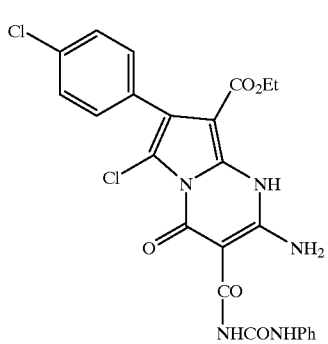

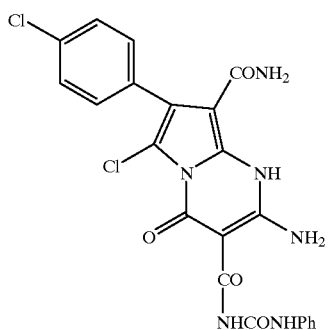 (C-26)
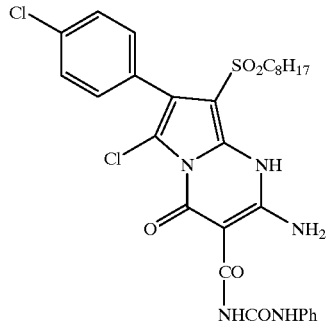 (C-30)
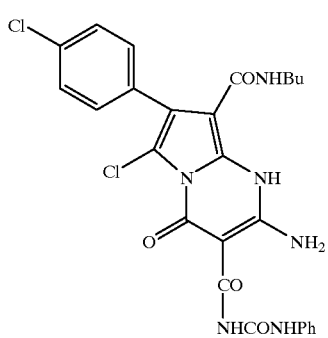 (C-27)
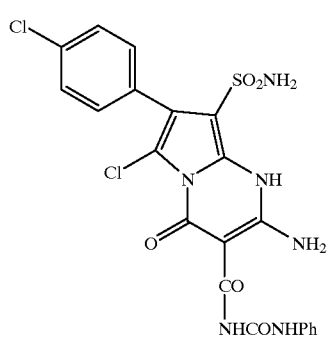 (C-31)
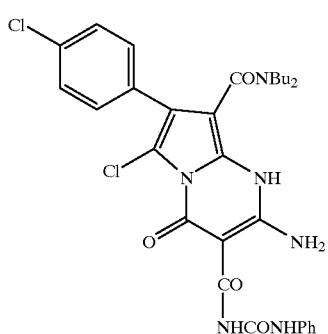 (C-28)
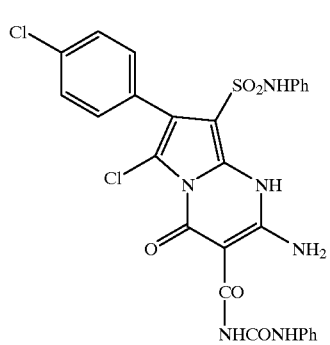 (C-32)
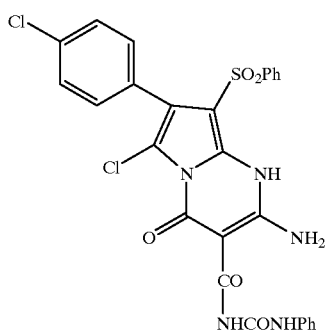 (C-29)
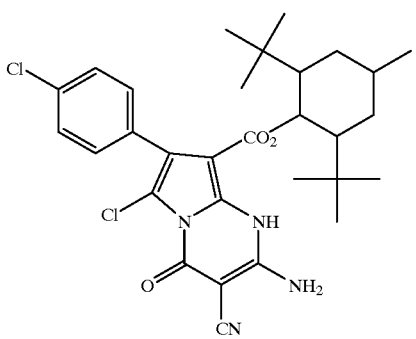 (C-33)

-continued (C-34) 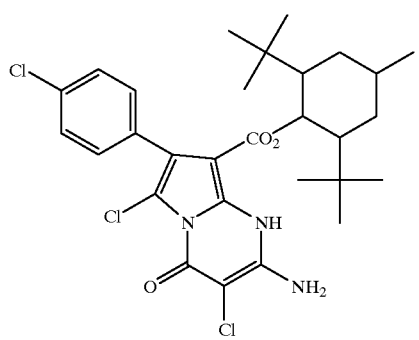

(C-35) 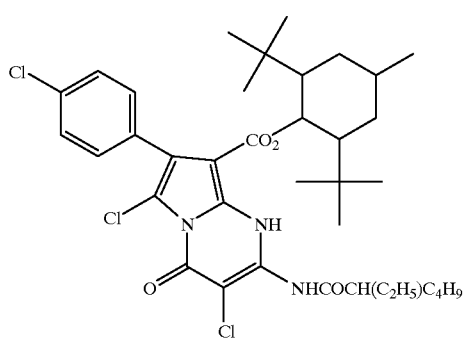

(C-36) 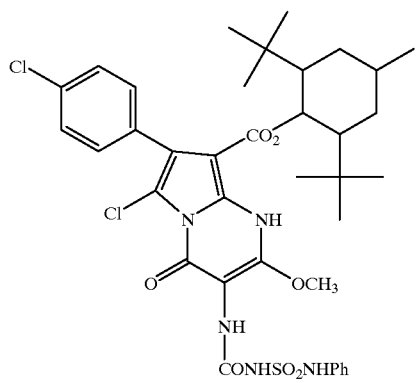

(C-37) 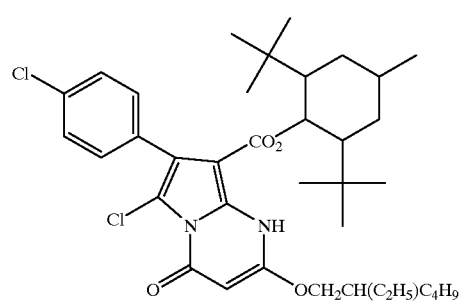

-continued (C-38) 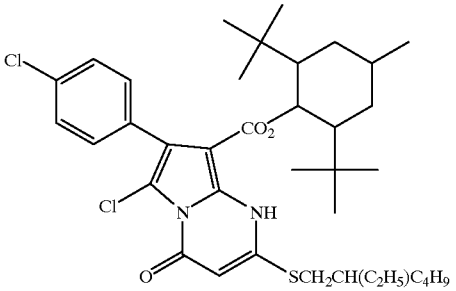

(C-39) 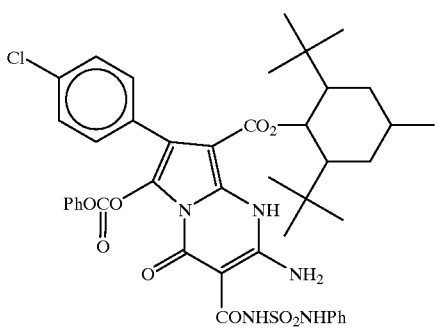

(C-40)

The details of the heat-sensitive recording material of the present invention are given below.

The heat-sensitive recording material of the present invention comprises a substrate and a heat-sensitive recording layer and, if necessary, other layers formed on the substrate.

[Heat-sensitive recording layer]

The heat-sensitive recording layer comprises a coupler and a diazonium salt, and, if necessary, other components.

(Coupler)

The coupler to be contained in the heat-sensitive recording layer is a pyrrolopyrimidineone compound represented by the general formula (1). The pyrrolopyrimidineone compounds may be used singly or in combination of two or more.

The coupler of the present invention is designed to undergo a coupling reaction with a diazo compound to form a dye in a basic environment and/or a neutral environment. According to purposes such as color adjustment, the coupler of the present invention can be used together with a known coupler. Examples of the couplers which can be used together with the coupler of the present invention include a so-called active methylene compound having a methylene group adjacent to a carbonyl group, a phenol derivative, and a naphthol derivative. The compounds exemplified below can be used in so far as these compounds meet the purpose of the present invention.

Particularly preferred examples of the couplers which can be used together with the coupler of the present invention include resorcinol, phloroglucinol, 2,3-dihydroxynaphthalene, sodium 2,3-dihydroxynaphthalene-6-sulfonate, 1-hydroxy-2-naphthoic acid morpholinopropylamide, sodium 2-hydroxy-3-naphthalenesulfonate, 2-hydroxy-3-naphthalenesulfonic acid anilide, 2-hydroxy-3-naphthalenesulfonic acid morpholinopropylamide, 2-hydroxy-3-naphthalenesulfonic acid-2-ethylhexyloxypropylamide, 2-hydroxy-3-naphthalenesulfonic acid-2-ethylhexylamide, 5-acetamido-1-naphthol, sodium 1-hydroxy-8-acetamidonaphthalene-3,6-disulfonate, 1-hydroxy-8-acetamidonaphthalene-3,6-disulfonic acid dianilide, 1,5-dihydroxynaphthalene, 2-hydroxy-3-naphthoic acid morpholinopropylamide, 2-hydroxy-3-naphthoic acid octylamide, 2-hydroxy-3-naphthoic acid anilide, 5,5-dimethyl-1,3-cyclohexanedione, 1,3-cyclopentanedione, 5-(2-n-tetradecyloxyphenyl)-1,3-cyclohexanedione, 5-phenyl-4-methoxycarbonyl-1,3-cyclohexanedione, 5-(2,5-di-n-octyloxyphenyl)-1,3-cyclohexanedione, N,N'-dicyclohexylbarbituric acid, N,N'-di-n-dodecylbarbituric acid, N-n-octyl-N'-n-octadecylbarbituric acid, N-phenyl-N'-(2,5-di-n-octyloxyphenyl)barbituric acid, N,N'-bis(octadecyloxycarbonylmethyl)barbituric acid, 1-phenyl-3-methyl-5-pyrazolone, 1-(2,4,6-trichlorophenyl)-3-anilino-5-pyrazolone, 1-(2,4,6-trichlorophenyl)-3-benzamido-5-pyrazolone, 6-hydroxy-4-methyl-3-cyano-1-(2-ethylhexyl)-2-pyridone, 2,4-bis(benzoylacetamido)toluene, 1,3-bis(pivaloylacetamidomethyl)benzene, benzoylacetonitrile, thenoylacetonitrile, acetoacetanilide, benzoylacetanilide, pivalolylacetanilide, 2-chloro-5-(N-n-butylsulfamoyl)-1-pivaloylacetamidobenzene, 1-(2-ethylhexyloxypropyl)-3-cyano-4-methyl-6-hydroxy-1,2-dihydropyridine-2-one, 1-(dodecyloxypropyl)-3-acetyl-4-methyl-6-hydroxy-1,2-dihydropyridine-2-one, 1-(4-n-octyloxyphenyl) -3-tert-butyl-5-aminopyrazole and the like.

Details of the couplers are described in, for example, JP-A Nos. 4-201,483; 7-223,367; 7-223,368; 7-323,660, Japanese Patent Application Nos. 5-278,608; 5-297,024; 6-18,669; 6-18,670; 7-316,280; 8-027,095; 8-027,096; 8-030,799; 8-12,610; 8-132,394; 8-358,755; 8-358,756, and 9-069,990.

The amount of the coupler to be used in the heat-sensitive layer, is in the range of 0.02 to 5 g/m². From the standpoint of effects, the amount is preferably in the range of 0.1 to 4 g/m². An amount less than 0.02 g/m² is not desirable from the standpoint of color formability, while an amount more than 5 g/m² is not desirable from the standpoint of coatability.

The coupler in the present invention can be used as a solid-state dispersion prepared by dispersing the coupler together with other components in the presence of a water-soluble polymer in a sand mill or the like. The coupler can also be used as an emulsion prepared by emulsifying the coupler in the presence of a suitable emulsifying aid. The solid-state dispersing method and the emulsifying method are not particularly limited, and methods hitherto known can be employed. The details of these methods are described in JP-A Nos. 59-190,886; 2-141,279; and 7-17,145.

(Diazonium salts)

The diazonium salt for use in the present invention is a compound represented by the following general formula:

$$Ar-N_2^+X^-$$

where Ar indicates the aromatic portion and $X^-$ indicates an acid anion. The compound undergoes a color forming coupling reaction with a coupler when heated. The compound is decomposed by light. The maximum absorption wavelength of the compound can be controlled by the position and type of the substituent group on the Ar portion.

Specific examples of the diazonium forming the salt include 4-(p-tolylthio)-2,5-dibutoxybenzenediazonium, 4-(4-chlorophenylthio)-2,5-dibutoxybenzenediazonium, 4-(N,N-dimethylamino)benzenediazonium, 4-(N,N-diethylamino)benzenediazonium, 4-(N,N-dipropylamino) benzenediazonium, 4-(N-methyl-N-benzylamino) benzenediazonium, 4-(N,N-dibenzylamino) benzenediazonium, 4-(N-ethyl-N-hydroxyethylamino) benzenediazonium, 4-(N,N-diethylamino)-3-methoxybenzenediazonium, 4-(N,N-dimethylamino)-2-methoxybenzenediazonium, 4-(N-benzoylamino)-2,5-diethoxybenzenediazonium, 4-morpholino-2,5-dibutoxybenzenediazonium, 4-anilinobenzenediazonium, 4-[N-(4-methoxybenzoyl)amino]-2,5-diethoxybenzenediazonium, 4-pyridino-3-ethylbenzenediazonium, 4-[N-(1-methyl-2-(4-methoxyphenoxy)ethyl)-N-hexylamino]-2-hexyloxybenzenediazonium, 4-[N-(2-(4-methoxyphenbxy) ethyl)-N-hexylamino]-2-hexyloxybenzenediazonium, 2-(1-ethylpropyloxy)-4-[di-(di-t-n-butylaminocarbonylmethyl) amino]benzenediazonium, 2-benzylsulfonyl-4-[N-methyl-N-(2-octanoyloxyethyl)]aminobenzenediazonium, and so on.

From the standpoint of effects, the maximum absorption wavelength $\lambda_{max}$ of the diazonium salt for use in the present invention is preferably 450 nm or less and more preferably 290 to 440 nm. If the diazonium salt has $\lambda_{max}$ on a longer wavelength side relative to the above-mentioned wavelength range, raw stock storability of the photosensitive material is adversely affected. On the other hand, if the diazonium salt has $\lambda_{max}$ on a shorter wavelength side relative to the above-mentioned wavelength range, image fixation, image storability, and hue in cyan color formation are adversely affected when combined with a coupler.

It is preferable that the diazonium salt for use in the present invention has a number of carbon atoms equal to or greater than 12, solubility in water of 1% or less, and solubility in ethyl acetate of 5% or more.

Among these diazonium salts, the use of the diazonium salts represented by the following general formulae (2) to (4) are more preferable from the standpoints of color hue of dye, image storability, and image fixation.

(2)

ArS—⟨benzene with OR¹¹ (top), N₂⁺X⁻ (right), R¹²O (bottom)⟩

(3)

R¹⁵\N/R¹⁶ —⟨benzene with OR¹⁴, N₂⁺X⁻, Y⟩

(4)

R¹⁸O—⟨benzene with OR¹⁷, N₂⁺X⁻⟩

(2)-1

CH₃—C₆H₄—S—⟨benzene: OC₄H₉(n-), N₂⁺PF₆⁻, n-C₄H₉O⟩

(2)-2

Cl—C₆H₄—S—⟨benzene: OC₄H₉(n-), N₂⁺PF₆⁻, n-C₄H₉O⟩

(2)-3

⟨2-CON(C₂H₅)₂-phenyl⟩—S—⟨benzene: OC₄H₉(n-), N₂⁺PF₆⁻, n-C₄H₉O⟩

(2)-4 n-C₄H₉CH(C₂H₅)CH₂S—⟨benzene: OC₄H₉(n-), N₂⁺PF₆⁻, n-C₄H₉O⟩

(3)-1

(n-C₆H₁₃)₂N—⟨benzene: OC₆H₁₃(n-), N₂⁺PF₆⁻⟩

(3)-2

4-CH₃O-C₆H₄-O-CH₂CH(CH₃)-N(n-C₆H₁₃)—⟨benzene: OC₆H₁₃(n-), N₂⁺PF₆⁻⟩

(3)-3

[(n-C₄H₉)₂NCOCH₂]₂N—⟨benzene: OCH(C₂H₅)₂, N₂⁺PF₆⁻⟩

(3)-4

[(n-C₈H₁₇)₂NCOCH₂]₂N—⟨benzene: OCH₃, N₂⁺PF₆⁻⟩

(3)-5

N[n-C₈H₁₇][(n-C₄H₉)₂NCOCH₂]—⟨benzene: OC₆H₁₃(n-), N₂⁺PF₆⁻⟩

(3)-6

(NC—CH₂CH₂)₂N—⟨benzene: OCH₂CH(C₂H₅)C₄H₉(n-), N₂⁺PF₆⁻⟩

(3)-7

(CH₃COCH₂CH₂)₂N—⟨benzene: OC₆H₁₃(n-), N₂⁺PF₆⁻⟩

(3)-8 morpholino—⟨benzene: OC₄H₉(n-), N₂⁺PF₆⁻, n-C₄H₉O⟩

(3)-9

4-[C₄H₉CH(C₂H₅)CO]-piperazin-1-yl—⟨benzene: OC₄H₉(n-), N₂⁺PF₆⁻, n-C₄H₉O⟩

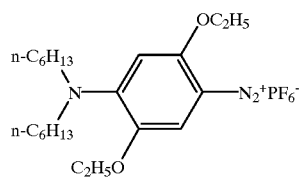

(3)-10

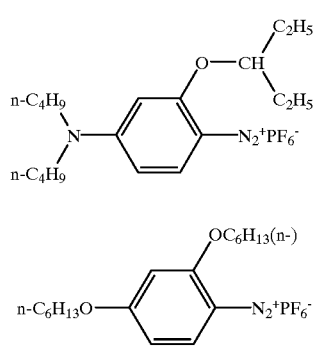

(3)-11

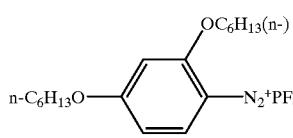

(4)-1

In the general formula (2), Ar represents a substituted or unsubstituted aryl group.

Examples of the substituent groups include an alkyl group, an alkoxy group, an alkylthio group, an aryl group, an aryloxy group, an arylthio group, an acyl group, an alkoxycarbonyl group, a carbamoyl group, a carboxylic acid amide group, a sulfonyl group, a sulfamoyl group, a sulfonamide group, a ureido group, a halogen group, an amino group, a heterocyclic group, and so on. These substituent groups may be further substituted.

The aryl group represented by Ar is preferably an aryl group having 6 to 30 carbon atoms. Examples of the aryl group include a phenyl group, a 2-methylphenyl group, a 2-chlorophenyl group, a 2-methoxyphenyl group, a 2-butoxyphenyl group, a 2-(2-ethylhexyloxy)phenyl group, a 2-octyloxyphenyl group, a 3-(2,4-di-t-pentylphenoxyethoxy)phenyl group, a 4-chlorophenyl group, a 2,5-dichlorophenyl group, a 2,4,6-trimethylphenyl group, a 3-chlorophenyl group, a 3-methylphenyl group, a 3-methoxyphenyl group, a 3-butoxyphenyl group, a 3-cyanophenyl group, a 3-(2-ethylhexyloxy)phenyl group, a 3,4-dichlorophenyl group, a 3,5-dichlorophenyl group, a 3,4-dimethoxyphenyl group, a 3-(dibutylaminocarbonylmethoxy)phenyl group, a 4-cyanophenyl group, a 4-methylphenyl group, a 4-methoxyphenyl group, a 4-butoxyphenyl group, a 4-(2-ethylhexyloxy)phenyl group, a 4-benzylphenyl group, a 4-aminosulfonylphenyl group, a 4-N,N-dibutylaminosulfonylphenyl group, a 4-ethoxycarbonylphenyl group, a 4-(2-ethylhexylcarbonyl)phenyl group, a 4-fluorophenyl group, a 3-acetylphenyl group, a 2-acetylaminophenyl group, a 4-(4-chlorophenylthio)phenyl group, a 4-(4-methylphenyl)thio-2,5-dibutoxyphenyl group, a 4-(N-benzyl-N-methylamino)-2-dodecyloxycarbonylphenyl group, and so on. It should be noted, however, that the aryl group is not limited to these groups. These groups may be further substituted by an alkyloxy group, an alkylthio group, a substituted phenyl group, a cyano group, a substituted amino group, a halogen atom, a heterocyclic group, and the like.

$R^{11}$ and $R^{12}$ each represents a substituted or unsubstituted alkyl group, or represents a substituted or unsubstituted aryl group. $R^{11}$ and $R^{12}$ may be the same or different.

Examples of the substituent group include an alkoxy group, an alkoxycarbonyl group, an alkylsulfonyl group, a substituted amino group, a substituted amido group, an aryl group, an aryloxy group, and so on. It should be noted, however, that the substituent group is not limited to these groups.

When $R^{11}$ and $R^{12}$ each represents an alkyl group, the alkyl group is preferably an alkyl group having 1 to 18 carbon atoms. Examples of the alkyl group include a methyl group, a trifluoromethyl group, an ethyl group, a propyl group, an isopropyl group, a butyl group, a sec-butyl group, a t-butyl group, a pentyl group, an isopentyl group, a cyclopentyl group, a hexyl group, a cyclohexyl group, an octyl group, a t-octyl group, a 2-ethylhexyl group, a nonyl group, an octadecyl group, a benzyl group, a 4-methoxybenzyl group, a triphenylmethyl group, an ethoxycarbonylmethyl group, a butoxycarbonylmethyl group, a 2-ethylhexyloxycarbonylmethyl group, a 2',4'-diisopentylphenyloxymethyl group, a 2',4'-di-t-butylphenyloxymethyl group, a dibenzylaminocarbonylmethyl group, a 2,4-di-t-amylphenyloxypropyl group, an ethoxycarbonylpropyl group, a 1-(2',4'-di-t-amylphenyloxy)propyl group, an acetylaminoethyl group, a 2-(N,N-dimethylamino)ethyl group, a 2-(N,N-diethylamino)propyl group, a methanesulfonylaminopropyl group and so on.

When $R^{11}$ and $R^{12}$ each represents an aryl group, the aryl group is preferably an aryl group having 6 to 30 carbon atoms. Examples of the aryl group include a phenyl group, a 2-methylphenyl group, a 2-chlorophenyl group, a 2-methoxyphenyl group, a 2-butoxyphenyl group, a 2-(2-ethylhexyloxy)phenyl group, a 2-octyloxyphenyl group, a 3-(2,4-di-t-pentylphenoxyethoxy)phenyl group, a 4-chlorophenyl group, a 2,5-dichlorophenyl group, a 2,4,6-trimethylphenyl group, a 3-chlorophenyl group, a 3-methylphenyl group, a 3-methoxyphenyl group, a 3-butoxyphenyl group, a 3-cyanophenyl group, a 3-(2-ethylhexyloxy)phenyl group, a 3,4-dichlorophenyl group, a 3,5-dichlorophenyl group, a 3,4-dimethoxyphenyl group, a 3-(dibutylaminocarbonylmethoxy)phenyl group, a 4-cyanophenyl group, a 4-methylphenyl group, a 4-methoxyphenyl group, a 4-butoxyphenyl group, a 4-(2-ethylhexyloxy)phenyl group, a 4-benzylphenyl group, a 4-aminosulfonylphenyl group, a 4-N,N-dibutylaminosulfonylphenyl group, a 4-ethoxycarbonylphenyl group, a 4-(2-ethylhexylcarbonyl)phenyl group, a 4-fluorophenyl group, a 3-acetylphenyl group, a 2-acetylaminophenyl group, a 4-(4-chlorophenylthio)phenyl group, a 4-(4-methylphenyl)thio-2,5-dibutoxyphenyl group, and a 4-(N-benzyl-N-methylamino)-2-dodecyloxycarbonylphenyl group, and so on. It should be noted, however, that the aryl group is not limited to these groups. These groups may be further substituted by an alkyloxy group, an alkylthio group, a substituted phenyl group, a cyano group, a substituted amino group, a halogen atom, a heterocyclic group, and the like.

In the general formula (3), $R^{14}$, $R^{15}$, and $R^{16}$ each represents a substituted or unsubstituted alkyl group, or represents a substituted or unsubstituted aryl group. $R^{14}$, $R^{15}$, and $R^{16}$ may be the same or different.

Examples of the substituent group include an alkyl group, an alkoxy group, an alkylthio group, an aryl group, an arylxoy group, an arylthio group, an acyl group, an alkoxycarbonyl group, a carbamoyl group, a carboxylic acid amido group, a sulfonyl group, a sulfamoyl group, a sulfonamide group, a ureido group, a halogen atom, an amino group, a heterocyclic group, and so on.

Where $R^{14}$, $R^{15}$, and $R^{16}$ each represents an alkyl group, the alkyl group is preferably an alkyl group having 1 to 18 carbon atoms. Examples of the alkyl group include a methyl group, a trifluoromethyl group, an ethyl group, a propyl group, an isopropyl group, a butyl group, a sec-butyl group, a t-butyl group, a pentyl group, an isopentyl group, a cyclopentyl group, a hexyl group, a cyclohexyl group, an octyl group, a t-octyl group, a 2-ethylhexyl group, a nonyl group, an octadecyl group, a benzyl group, a 4-methoxybenzyl group, a triphenylmethyl group, an ethoxycarbonylmethyl group, a butoxycarbonylmethyl group, a 2-ethylhexyloxycarbonylmethyl group, a 2',4'-diisopentylphenyloxymethyl group, a 2',4'-di-t-butylphenyloxymethyl group, a dibenzylaminocarbonylmethyl group, a 2,4-di-t-amylphenyloxypropyl group, an ethoxycarbonylpropyl group, a 1-(2',4'-di-t-amylphenyloxy)propyl group, an acetylaminoethyl group, a 2-(N,N-dimethylamino)ethyl group, a 2-(N,N-diethylamino)propyl group, a methanesulfonylaminopropyl group, a 1-methyl-2-(4-methoxyphenoxy)ethyl group, a di-n-butylaminocarbonylmethyl group, a di-n-octylaminocarbonylmethyl group, and so on.

When $R^{14}$, $R^{15}$, and $R^{16}$ each represents an aryl group, the aryl group is preferably an aryl group having 6 to 30 carbon atoms. Examples of the aryl group include a phenyl group, a 2-methylphenyl group, a 2-chlorophenyl group, a 2-methoxyphenyl group, a 2-butoxyphenyl group, a 2-(2-ethylhexyloxy)phenyl group, a 2-octyloxyphenyl group, a 3-(2,4-di-t-pentylphenoxyethoxy)phenyl group, a 4-chlorophenyl group, a 2,5-dichlorophenyl group, a 2,4,6-trimethylphenyl group, a 3-chlorophenyl group, a 3-methylphenyl group, a 3-methoxyphenyl group, a 3-butoxyphenyl group, a 3-cyanophenyl group, a 3-(2-ethylhexyloxy)phenyl group, a 3,4-dichlorophenyl group, a 3,5-dichlorophenyl group, a 3,4-dimethoxyphenyl group, a 3-(dibutylaminocarbonylmethoxy)phenyl group, a 4-cyanophenyl group, a 4-methylphenyl group, a 4-methoxyphenyl group, a 4-butoxyphenyl group, a 4-(2-ethylhexyloxy)phenyl group, a 4-benzylphenyl group, a 4-aminosulfonylphenyl group, a 4-N,N-dibutylaminosulfonylphenyl group, a 4-ethoxycarbonylphenyl group, a 4-(2-ethylhexylcarbonyl)phenyl group, a 4-fluorophenyl group, a 3-acetylphenyl group, a 2-acetylaminophenyl group, a 4-(4-chlorophenylthio)phenyl group, a 4-(4-methylphenyl)thio-2,5-dibutoxyphenyl group, and a 4-(N-benzyl-N-methylamino)-2-dodecyloxycarbonylphenyl group, and so on. It should be noted, however, that the aryl group is not limited to these groups. These groups may be further substituted by an alkyloxy group, an alkylthio group, a substituted phenyl group, a cyano group, a substituted amino group, a halogen atom, a heterocyclic group, or the like.

In the general formula (3), Y represents a hydrogen atom or a —$OR^{13}$ group. In the —$OR^{13}$ group, $R^{13}$ represents a substituted or unsubstituted alkyl group, or represents a substituted or unsubstituted aryl group.

Examples of the substituent group include an alkyl group, an alkoxy group, an alkylthio group, an aryl group, an arylxoy group, an arylthio group, an acyl group, an alkoxycarbonyl group, a carbamoyl group, a carboxylic acid amido group, a sulfonyl group, a sulfamoyl group, a sulfonamide group, a ureido group, a halogen atom, an amino group, a heterocyclic group, and soon. From the standpoint of adjusting color hue, Y is preferably a hydrogen atom or an alkyloxy group in which $R^{13}$ is an alkyl group.

When $R^{13}$ in —$OR^{13}$ represents an alkyl group, the alkyl group is preferably an alkyl group having 1 to 18 carbon atoms. Examples of the alkyl group include a methyl group, a trifluoromethyl group, an ethyl group, a propyl group, an isopropyl group, a butyl group, a sec-butyl group, a t-butyl group, a pentyl group, an isopentyl group, a cyclopentyl group, a hexyl group, a cyclohexyl group, an octyl group, a t-octyl group, a 2-ethylhexyl group, a nonyl group, an octadecyl group, a benzyl group, a 4-methoxybenzyl group, a triphenylmethyl group, an ethoxycarbonylmethyl group, a butoxycarbonylmethyl group, a 2-ethylhexyloxycarbonylmethyl group, a 2',4'-diisopentylphenyloxymethyl group, a 2',4'-di-t-butylphenyloxymethyl group, a dibenzylaminocarbonylmethyl group, a 2,4-di-t-amylphenyloxypropyl group, an ethoxycarbonylpropyl group, a 1-(2',4'-di-t-amylphenyloxy)propyl group, an acetylaminoethyl group, a 2-(N,N-dimethylamino)ethyl group, a 2-(N,N-diethylamino)propyl group, a methanesulfonylaminopropyl group, and so on.

When $R^{13}$ in —$OR^{13}$ represents an aryl group, the aryl group is preferably an aryl group having 6 to 30 carbon atoms. Examples of the aryl group include a phenyl group, a 2-methylphenyl group, a 2-chlorophenyl group, a 2-methoxyphenyl group, a 2-butoxyphenyl group, a 2-(2-ethylhexyloxy)phenyl group, a 2-octyloxyphenyl group, a 3-(2,4-di-t-pentylphenoxyethoxy)phenyl group, a 4-chlorophenyl group, a 2,5-dichlorophenyl group, a 2,4,6-trimethylphenyl group, a 3-chlorophenyl group, a 3-methylphenyl group, a 3-methoxyphenyl group, a 3-butoxyphenyl group, a 3-cyanophenyl group, a 3-(2-ethylhexyloxy)phenyl group, a 3,4-dichlorophenyl group, a 3,5-dichlorophenyl group, a 3,4-dimethoxyphenyl group, a 3-(dibutylaminocarbonylmethoxy)phenyl group, a 4-cyanophenyl group, a 4-methylphenyl group, a 4-methoxyphenyl group, a 4-butoxyphenyl group, a 4-(2-ethylhexyloxy)phenyl group, a 4-benzylphenyl group, a 4-aminosulfonylphenyl group, a 4-N,N-dibutylaminosulfonylphenyl group, a 4-ethoxycarbonylphenyl group, a 4-(2-ethylhexylcarbonyl)phenyl group, a 4-fluorophenyl group, a 3-acetylphenyl group, a 2-acetylaminophenyl group, a 4-(4-chlorophenylthio)phenyl group, a 4-(4-methylphenyl)thio-2,5-dibutoxyphenyl group, and a 4-(N-benzyl-N-methylamino)-2-dodecyloxycarbonylphenyl group, and so on. It should be noted, however, that the aryl group is not limited to these groups. These groups may be further substituted by an alkyloxy group, an alkylthio group, a substituted phenyl group, a cyano group, a substituted amino group, a halogen atom, a heterocyclic group, or the like.

In the general formula (4), $R^{17}$ and $R^{18}$ each represents a substituted or unsubstituted alkyl group, or represents a substituted or unsubstituted aryl group. $R^{17}$ and $R^{18}$ may be the same or different.

Examples of the substituent group include an alkyl group, an alkoxy group, an alkylthio group, an aryl group, an arylxoy group, an arylthio group, an acyl group, an alkoxycarbonyl group, a carbamoyl group, a carboxylic acid amido group, a sulfonyl group, a sulfamoyl group, a sulfonamide group, a ureido group, a halogen atom, an amino group, a heterocyclic group, and so on.

When $R^{17}$ and $R^{18}$ each represents an alkyl group, the alkyl group is preferably an alkyl group having 1 to 18 carbon atoms. Examples of the alkyl group include a methyl group, a trifluoromethyl group, an ethyl group, a propyl group, an isopropyl group, a butyl group, a sec-butyl group, a t-butyl group, a pentyl group, an isopentyl group, a cyclopentyl group, a hexyl group, a cyclohexyl group, an octyl group, a t-octyl group, a 2-ethylhexyl group, a nonyl group, an octadecyl group, a benzyl group, a 4-methoxybenzyl group, a triphenylmethyl group, an ethoxycarbonylmethyl group, a butoxycarbonylmethyl group, a 2-ethylhexyloxycarbonylmethyl group, a 2',4'-diisopentylphenyloxymethyl group, a 2',4'-di-t-butylphenyloxymethyl group, a dibenzylaminocarbonylmethyl group, a 2,4-di-t-amylphenyloxypropyl group, an ethoxycarbonylpropyl group, a 1-(2',4'-di-t-amylphenyloxy)propyl group, an acetylaminoethyl group, a 2-(N,N-dimethylamino)ethyl group, a 2-(N,N-diethylamino)propyl group, a methanesulfonylaminopropyl group, and so on. It should be noted, however, that the alkyl group is not limited to these groups.

When $R^{17}$ and $R^{18}$ each represents an aryl group, the aryl group is preferably an aryl group having 6 to 30 carbon atoms. Examples of the aryl group include a phenyl group, a 2-methylphenyl group, a 2-chlorophenyl group, a 2-methoxyphenyl group, a 2-butoxyphenyl group, a 2-(2-ethylhexyloxy)phenyl group, a 2-octyloxyphenyl group, a 3-(2,4-di-t-pentylphenoxyethoxy)phenyl group, a 4-chlorophenyl group, a 2,5-dichlorophenyl group, a 2,4,6-trimethylphenyl group, a 3-chlorophenyl group, a 3-methylphenyl group, a 3-methoxyphenyl group, a 3-butoxyphenyl group, a 3-cyanophenyl group, a 3-(2-ethylhexyloxy)phenyl group, a 3,4-dichlorophenyl group, a 3,5-dichlorophenyl group, a 3,4-dimethoxyphenyl group, a 3-(dibutylaminocarbonylmethoxy)phenyl group, a 4-cyanophenyl group, a 4-methylphenyl group, a 4-methoxyphenyl group, a 4-butoxyphenyl group, a 4-(2-ethylhexyloxy)phenyl group, a 4-benzylphenyl group, a 4-aminosulfonylphenyl group, a 4-N,N-dibutylaminosulfonylphenyl group, a 4-ethoxycarbonylphenyl group, a 4-(2-ethylhexylcarbonyl)phenyl group, a 4-fluorophenyl group, a 3-acetylphenyl group, a 2-acetylaminophenyl group, a 4-(4-chlorophenylthio)phenyl group, a 4-(4-methylphenyl)thio-2,5-dibutoxyphenyl group, and a 4-(N-benzyl-N-methylamino)-2-dodecyloxycarbonylphenyl group, and so on. These groups may be further substituted by an alkyloxy group, an alkylthio group, a substituted phenyl group, a cyano group, a substituted amino group, a halogen atom, a heterocyclic group, and the like.

In the general formulae (2) to (4), X⁻ represents an acid anion. Examples of the acid anion include a polyfluoroalkylcarboxylic acid having 1 to 9 carbon atoms, a polyfluoroalkylsulfonic acid having 1 to 9 carbon atoms, boron tetrafluoride, tetraphenylboron, hexafluorophosphoric acid, an aromatic carboxylic acid, an aromatic sulfonic acid, and so on. Hexafluorophosphoric acid is preferable from the standpoint of crystallinity.

Specific examples of the diazonium salts represented by the general formulae (2) to (4) are given below. It should be noted, however, that the present invention is not limited to these compounds.

(2)-1

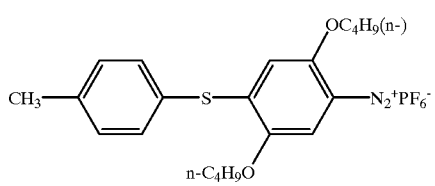

(2)-2

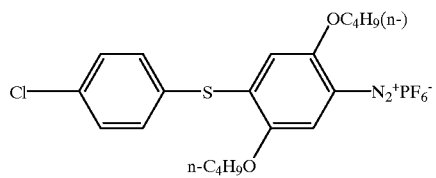

(2)-3

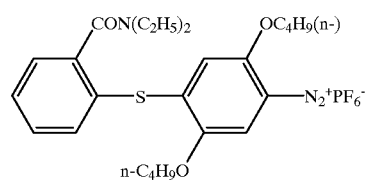

(2)-4

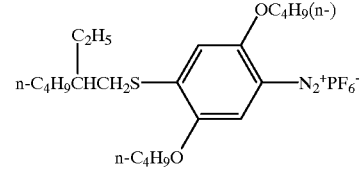

(3)-1

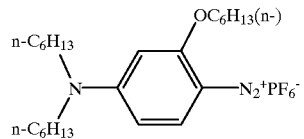

(3)-2

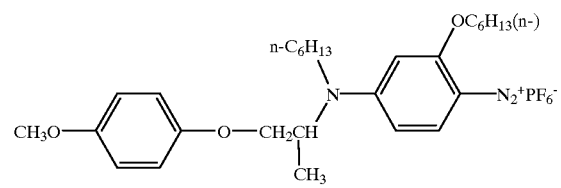

(3)-3

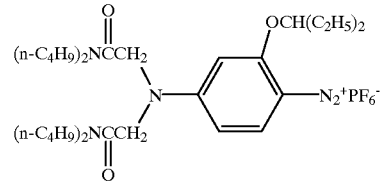

(3)-4

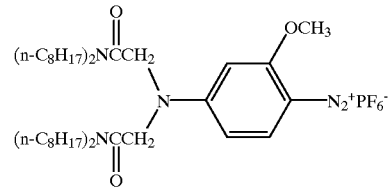

(3)-5

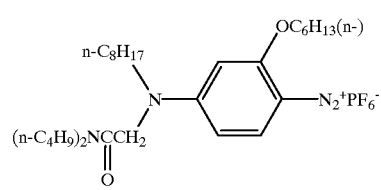

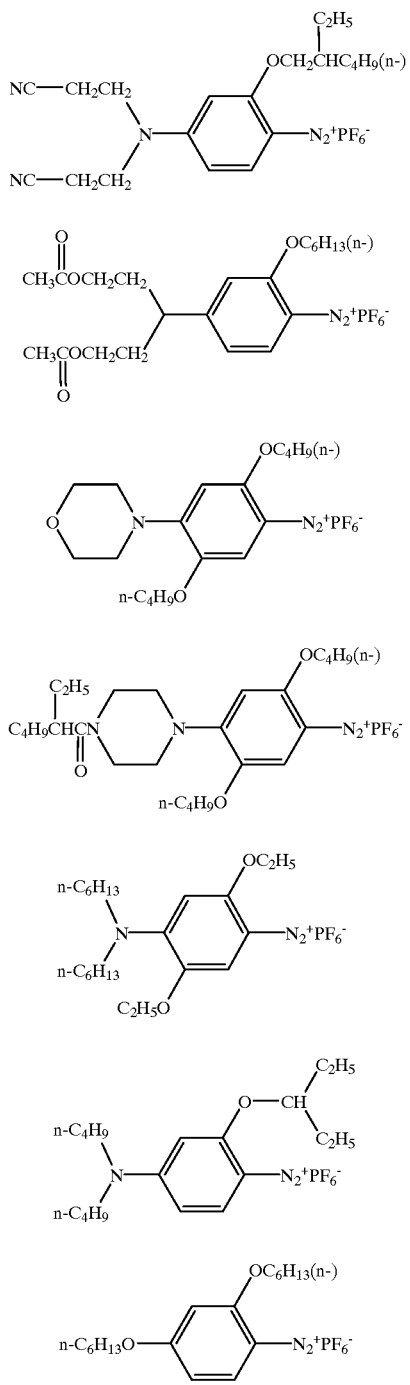

diazo compound in microcapsules. The method for forming the microcapsules is not particularly limited. The microcapsules can be formed by a conventionally known method using a wall forming material such as gelatin, polyurea, polyurethane, polyimide, polyester, polycarbonate, melamine, or the like. Among these wall forming materials, polyurethane and polyurea are preferable from the standpoints of color formation and storability. Details of the method for forming the microcapsules are described in, for example, JP-A No. 2-141,279.

When forming the microcapsules, an organic solvent having a high boiling point may be used as a solvent for dispersing the diazonium salt. The organic solvent is not particularly limited, and a conventionally known organic, solvent such as an alkyl phthalate, a phosphate, a citrate, a benzoate, an alkyl amide, an aliphatic ester, and a trimesate, may be used.

(Other components)

In order to accelerate the coupling reaction, it is preferable that an organic base, such as a tertiary amine, a piperidine, a piperazine, an amidine, a formamidine, a pyridine, a guanidine, and a morpholine, is used in the present invention.

Specific examples of the organic base include piperazines such as N,N'-bis(3-phenoxy-2-hydroxypropyl)piperazine, N,N'-bis[3-(p-methylphenoxy)-2-hydroxypropyl]piperazine, N,N'-bis[3-(p-methoxyphenoxy)-2-hydroxypropyl]piperazine, N,N'-bis(3-phenylthio-2-hydroxypropyl)piperazine, N,N'-bis[3-(β-naphthoxy)-2-hydroxypropyl]piperazine, N-3-(β-naphthoxy)-2-hydroxypropyl-N'-methylpiperazine, and 1,4-bis{[3-(N-methylpiperazino)-2-hydroxy]propyloxy}benzene; morpholine such as N-(3-(,2-naphthoxy)-2-hydroxy]propylmorpholine, 1,4-bis[(3-morpholino-2-hydroxy)propyloxy]benzene, and 1,3-bis[(3-morpholino-2-hydroxy)propyloxy]benzene; piperidines such as N-(3-phenoxy-2-hydroxypropyl)piperidine and N-dodecylpiperidine; triphenylguanidine, tricyclohexylguanidine, dicyclohexylguanidine, 2-N-methyl-N-benzylaminoethyl 4-hydroxybenzoate, 2-N,N-di-n-butylaminoethyl 4-hydroxybenzoate, 4-(3-N,N-dibutylaminopropoxy)benzenesulfonamide, 4-(2-N,N-dibutylaminoethoxycarbonyl)phenoxyacetic acid amide, and so on.

Details of the organic base are described in, for example, JP-A Nos. 57-123,086; 60-49,991; and 60-94,381, and Japanese Patent Application Nos. 7-228,731; 7-235,157; and 7-235,158.

The following bases are also preferably used in the present invention.

(B-1)

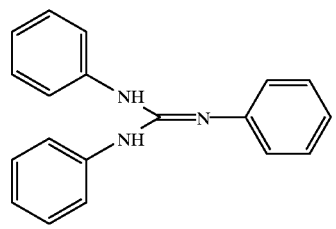

In the present invention, the diazonium salts represented by the general formulae (2) to (4) may be used singly or in combination of two or more. Further, depending on purposes such as adjustment of color hue, the diazonium salts represented by the general formulae (2) to (4) may be used in combination with conventional diazonium salts.

The diazonium salt used in the present invention is preferably contained in the heat-sensitive recording layer in an amount in the range of 0.02 to 3 g/m² and more preferably in the range of 0.1 to 2 g/m².

In order to improve the storability of the diazonium salt for use in the present invention, it is desirable to enclose the -continued (B-2)
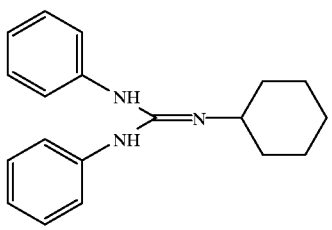

(B-3)
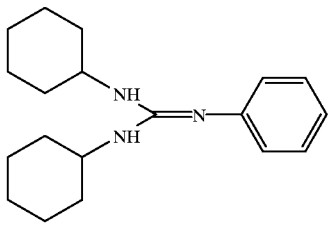

(B-4)
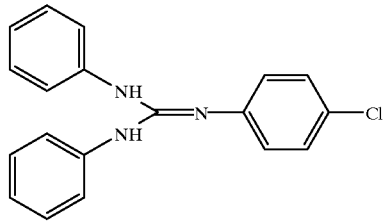

(B-5)
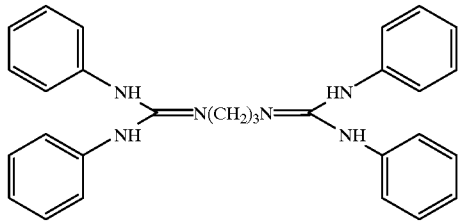

(B-6)
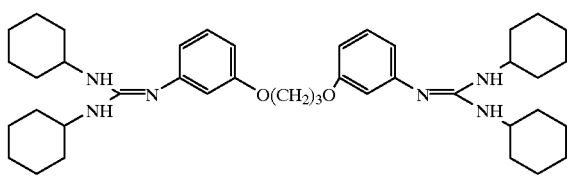

(B-7)
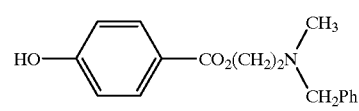

(B-8)
(n-C$_8$H$_{17}$)$_3$N (B-9)
(t-C$_8$H$_{17}$)$_3$N

These organic bases may be used singly or in combinations of two or more. Although the amount of the organic base for use in the present invention is not particularly limited, an amount in the range of 1 to 30 moles per mole of the diazonium salt compound is preferably used.

In the present invention., besides the pyrrolopyrimidine-one compounds represented by the general formula (1), a color forming aid can be added to the heat-sensitive recording layer in order to accelerate the 3; color forming reaction. Examples of the color forming aid include phenol derivatives, naphthol derivatives, alkoxy-substituted benzenes, alkoxy-substituted naphthalenes, hydroxyl compounds, carboxylic acid amides, sulfonamides, and so on. These compounds are believed to provide a high coloration density by lowering the melting points of the couplers or the bases or by improving the heat transmissivity of the microcapsule wall.

Further, in the present invention, the heat-sensitive recording layer preferably contains any of the reducing agents indicated below.

(R-1)
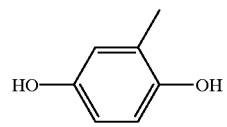

(R-2)
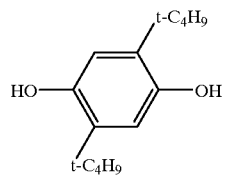

(R-3)
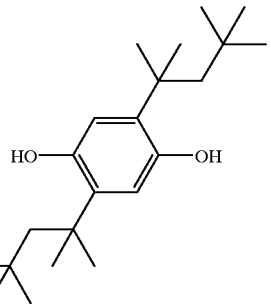

(R-4)
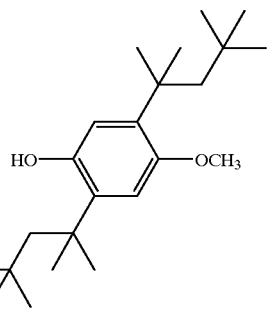

(R-5)
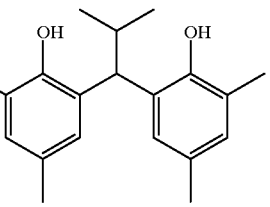

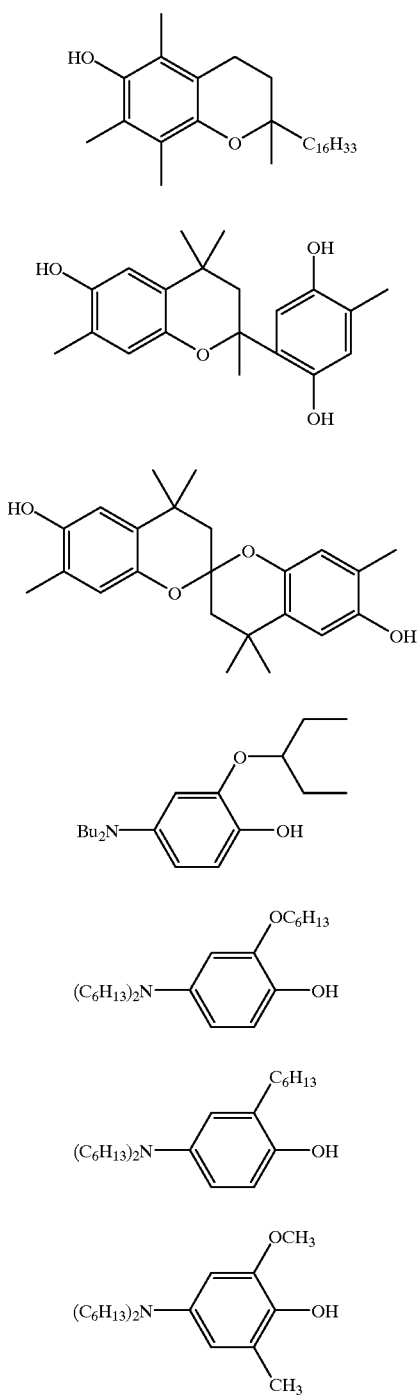

(R-6)
(R-7)
(R-8)
(R-9)
(R-10)
(R-11)
(R-12)

(Method for forming the heat-sensitive recording layer)

When forming the heat-sensitive recording layer in the heat-sensitive recording material of the present invention, a coating liquid, which comprises a diazonium compound, a pyrrolopyrimidineone compound represented by the general formula (1), and other additives, is first prepared. The coating liquid is then applied onto a substrate, such as a paper, a synthetic resin film, or the like, by such method as bar coating, blade coating, air knife coating, gravure coating, roll coating, spraying, dipping, or curtain coating. After that, the coating layer is dried to thereby form a heat-sensitive layer having a solid content in the range of 2 to 30 g m².

The binder for use in the present invention is not particularly limited. Therefore, a conventionally known binder can be used. Specific examples of the binder include polyvinyl alcohol, hydroxyethyl cellulose, methyl cellulose, carboxymethyl cellulose, gelatin, a styrene/acrylic acid copolymer, and so on. Details of the binder are described in, for example, JP-A No. 2-141,279. Further, organic or inorganic pigments, stabilizers, an antioxidant, and so on may be added if necessary.

In the heat-sensitive recording material of the present invention, the diazonium salt, the pyrrolopyrimidineone compound represented by the general formula (1), and so on may be contained in the same layer, or in different layers to thereby form a laminate structure.

[Substrate]

A substrate for use in the present invention may be a conventionally known substrate. Examples of the substrate include neutral paper, acidic paper, regenerated paper, paper laminated with a polyolefinic resin, synthetic paper, polyester film, film of a cellulosic derivative such as cellulose triacetate, polystyrene film, film of polyolefin such as polypropylene and polyethylene, and so on. These may be used singly or as a laminate of two or more of them.

A substrate having a thickness of 20 to 200 μm is used. It is also possible to form an intermediate layer between the substrate and the heat-sensitive recording layer. These are described in, for example, JP-A No. 61-54,980.

[Other layers]

It is preferable that a protective layer is formed on the heat-sensitive recording layer in the heat-sensitive recording material of the present invention. It is further desirable that the protective layer is laminated to the heat-sensitive recording layer. The protective layer is composed of a water-soluble polymeric compound, a pigment, and so on. In order to obtain both lightfastness and photo-fixation properties, the protective layer preferably contains a compound having the function of adjusting ultraviolet light transmissivity. A heat-sensitive recording material containing a compound which has the function of adjusting ultraviolet light transmissivity is described in JP-A No. 7-276,808.

The heat-sensitive recording material of the present invention can be used as a multicolor heat-sensitive recording material. The multicolor heat-sensitive recording material (heat-sensitive recording material) is described in, for example, JP-A Nos. 4-135,787; 4-144,784; 4-144,785; 4-194,842; 4-247,447; 4-247,448; 4-340,540; 4-340,541; and 5-34,860.

Specifically, the multicolor heat-sensitive recording material can be obtained by the lamination of heat-sensitive recording layers producing different color hues. Although the layer construction is not particularly limited, an example of the multicolor heat-sensitive recording material is formed in the following way. Two heat-sensitive recording layers (layer B and layer C), each of which contains a diazonium salt compound sensitive to different wavelengths along with a coupler capable of reacting with respective diazonium salt compounds when heated to thereby produce different color hues, and a heat-sensitive recording layer (layer A), which contains an electron donating colorless dye and an electron accepting compound, are laminated together.

More specifically, the multicolor heat-sensitive recording material comprises a substrate having thereon a first heat-sensitive recording layer (layer A), which contains an electron donating colorless dye and an electron accepting compound, a second heat-sensitive recording layer (layer B), which contains a diazonium salt compound whose maximum absorption wavelength is 360±20 nm and a coupler capable of reacting with the diazonium salt compound when heated to thereby produce a color hue, and a third heat-sensitive recording layer (layer C) which contains a diazonium salt compound whose maximum absorption wavelength is 400±20 nm and a coupler capable of reacting with the diazonium salt compound when heated to thereby produce a color hue. In this case, image recording in full color is possible if the color hues to be produced in the heat-sensitive recording layers are selected so as to provide three primary colors, i.e., yellow, magenta, and cyan, in the subtractive color mixing.

According to the recording method using this multicolor heat-sensitive recording material, the third heat-sensitive recording layer (layer C) is first heated so that the diazonium salt compound and the coupler contained in the layer react with each other to produce a color. Next, the material is irradiated with light of 400±20 nm in order to decompose the diazonium salt contained in layer C so that photo-fixation is carried out. The second heat-sensitive recording layer (layer B) is then colored by being heated sufficiently to allow the diazonium salt compound and the coupler contained in the layer to react with each other to produce a color. In this case, although layer C is also strongly heated simultaneously, layer C produces no color because the color forming ability of layer C is already lost due to decomposition (photo-fixation). Further, the material is irradiated with light of 360±20 nm in order to decompose the diazonium salt contained in layer B. Finally, the first heat-sensitive recording layer (layer A) is colored by being heated sufficiently to allow color formation. In this case, although the heat-sensitive recording layers C and B are also strongly heated simultaneously, these layers produce no color because the color forming ability of these layers is lost due to the already completed decomposition of the diazonium salts.

Alternatively, all of the heat-sensitive layers (i.e., layer A, layer B, and layer C in that order from above) may be composed of heat-sensitive layers each comprising a diazonium salt compound sensitive to different wavelengths in along with a coupler capable of reacting with the respective diazonium salt compounds when heated to thereby produce different color hues. In particular, by making the yellow layer which has a low luminosity factor the lowermost layer, the influence due to substrate surface roughness on images is reduced and, as a result, the image quality can be upgraded. In the case where all of the heat-sensitive layers (i.e., layer A, layer B, and layer C) are heat-sensitive layers comprising diazonium salt compounds, layer A and layer B need to be photo-fixed after color formation. The photo-fixation of layer C is not necessary.

Examples of the light source for use in the above-described photo-fixation include a fluorescent lamp, a xenon lamp, a mercury lamp, and so on. From the standpoint of efficient photo-fixation, the spectrum of the light is preferably nearly the same as that of the absorption spectrum of the diazo compound contained in the heat-sensitive recording material.

When the heat-sensitive recording material of the present invention is used for recording, the recording material may be used as a heat development-type photosensitive material which provides images by a process which includes optically exposing the material through an original to thereby decompose the diazonium salt compound except in the image forming region, and to form a latent image, and heating the entire material so that images are produced by heat development.

EXAMPLES

In order to further illustrate the present invention, the following examples are given, it being understood that the same are intended to be only illustrative and are in no wise limitative. "Part" in the examples always indicates "part by weight".

[A pyrrolopyrimidineone compound represented by the general formula (1)]

Example 1

[Synthesis of the exemplary compound C-2]

150 g (0.212 mol) of 2-amino-3-phenylaminosulfonylcarbamoyl-7-(4-chlorophenyl)-8-(2,6-di-t-butyl-4-methyl)cyclohexyloxycarbonyl-pyrrolo[1,2-a]pyrimidine was completely dissolved in a solvent mixture composed of 1.1 L of chloroform and 0.25 L of methanol at room temperature. 31.1 g (0.233 mol) of N-chlorosuccinic acid imide was added to the solution obtained and the resulting mixture was stirred for 3 hours at room temperature. After that, the reaction solution obtained was concentrated. Then, 1.0 L of water was added to the concentrated solution, and the reaction product was extracted with 1.5 L of ethyl acetate. The organic layer was washed twice with a saturated aqueous solution of sodium chloride, and thereafter dried by using magnesium sulfate. After removal by filtration of the magnesium sulfate, the organic layer was concentrated. Next, crystals were deposited by adding methanol to the organic layer. The crystals deposited were filtrated and washed with methanol. The crystals were then dried for 24 hours at room temperature. In this way, 105 g (0.141 mol, 67% yield) of 2-amino-3-phenylaminosulfonylcarbamoyl-6-chloro-7-(4-chlorophenyl)-8-(2,6-di-t-butyl-4-methyl) cyclohexyloxycarbonyl-pyrrolo[1,2-a]pyrimidine was obtained.

The melting point thereof was 210 to 213° C. The result of $^1$H-NMR(CDCl$_3$, 300 MHz) analysis was δ 7.58 (s, 1H), 7.41 (d, 2H), 7.31 (d, 2H), 7.20–7.25 (m, 3H), 7.14 (d, 2H), 5.80 (s, 1H), 1.12–1.35 (m), 0.95–1.05 (m), 0.77 (s, 21H), 0.42–0.58 (m). The result of Mass (DI) was 742.5; 649.8; 587.9; 534.0; 439.8; 360.0; 317.2; 275.2; 171.5.

Example 2

[Synthesis of the exemplary compound C-3]

7.77 g (9.87 mmol, 70% yield) of 2-amino-3-phenylaminosulfonylcarbamoyl-6-bromo-7-(4-chlorophenyl)-8-(2,6-di-t-butyl-4-methyl) cyclohexyloxycarbonyl-pyrrolo[1,2-a]pyrimidine was obtained by carrying out the same procedure as that in Example 1, except that 10 g (14.1 mmol) of 2-amino-3-phenylaminosulfonylcarbamoyl-7-(4-chlorophenyl)-8-(2,6-di-t-butyl-4-methyl)cyclohexyloxycarbonyl-pyrrolo[1,2-a] pyrimidine, 40 mL of chloroform, 10 mL of methanol, and 2.77 g(15.5 mmol) of N-bromosuccinic acid imide instead of 31.1 g of N-chlorosuccinic acid imide were used.

The melting point was 225 to 228° C. The result of $^1$H-NMR(CDCl$_3$, 300 MHz) analysis was δ 7.55 (s, 1H), 7.40 (d, 2H), 7.30 (d, 2H), 7.18–7.27 (m, 3H), 7.12 (d, 2H), 5.80 (s, 1H), 1.12–1.35 (m), 0.95–1.05 (m), 0.77 (s, 21H), 0.42–0.58 (m). The result of Mass (DI) was 787.1; 693.7; 552.1; 485.8; 406.1; 326.2; 241.5; 171.5.

Example 3

[Synthesis of the exemplary compound C-4]

1.42 g (1.70 mmol, 40% yield) of 2-amino-3-phenylaminosulfonylcarbamoyl-6-iodo-7-(4-chlorophenyl)-8-(2,6-di-t-butyl-4-methyl)cyclohexyloxycarbonyl-pyrrolo [1,2-a]pyrimidine was obtained by carrying out the same procedure as that in Example 1, except that 3.0 g (4.24 mmol) of 2-amino-3-phenylaminosulfonylcarbamoyl-7-(4-chlorophenyl)-8-(2,6-di-t-butyl-4-methyl)

cyclohexyloxycarbonyl-pyrrolo[1,2-a]pyrimidine, 30 mL of chloroform, 8 mL of methanol, and 1.05 g(4.66 mmol) of N-iodosuccinic acid imide instead of 31.1 g of N-chlorosuccinic acid imide were used.

The result of $^1$H-NMR(CDCl$_3$, 300 MHz) analysis was δ 7.42 (d, 2H), 7.30 (dd, 2H), 7.20–7.25 (m, 3H), 7.10 (d, 2H), 5.81 (s, 1H), 1.12–1.35(m), 0.95–1.05(m), 0.77 (s, 21H), 0.42–0.58 (m).

Example 4

[Synthesis of the exemplary compound C-1]

0.93 g (1.27 mmol, 30% yield) of 2-amino-3-phenylaminosulfonylcarbamoyl-6-fluoro-7-(4-chlorophenyl)-8-(2,6-di-t-butyl-4-methyl)cyclohexyloxycarbonyl-pyrrolo[1,2-a]pyrimidine was obtained by carrying out the same procedure as that in Example 1, except that 3.0 g (4.24 mmol) of 2-amino-3-phenylaminosulfonylcarbamoyl-7-(4-chlorophenyl)-8-(2,6-di-t-butyl-4-methyl)cyclohexyloxycarbonyl-pyrrolo(1,2-a]pyrimidine, 30 mL of chloroform, and 1.14 g(4.66 mmol) of N-fluoro-5-(trifluoromethyl) pyridinium-2-sulfonate (MEC-03 manufactured by Daikin Chemicals Sales Co., Ltd.) instead of 31.1 g of N-chlorosuccinic acid imide were used.

The result of $^1$H-NMR(CDCl$_3$, 300 MHz) analysis was δ 7.81 (d, 1H), 7.20–7.40 (m, 9H), 5.80 (s, 1H), 1.12–1.35 (m), 0.95–1.05 (m), 0.77 (s, 21H), 0.42–0.58 (m).

Example 5

[Synthesis of the exemplary compound C-13]

23.0 g (39.1 mol, 72% yield) of 2-amino-3-acyl-6-chloro-7-(4-chlorophenyl)-8-(2,6-di-t-butyl- 4-methyl)cyclohexyloxycarbonyl-pyrrolo[1,2-a]pyrimidine was obtained by carrying out the same procedure as that in Example 1, except that 30.0 g(54.2 mmol) of 2-amino-3-acyl-7-(4-chlorophenyl)-8-(2,6-di-t-butyl-4-methyl)cyclohexyloxycarbonyl-pyrrolo[1,2-a]pyrimidine instead of 2-amino-3-phenylaminosulfonylcarbamoyl-7-(4-chlorophenyl)-8-(2,6-di-t-butyl-4-methyl)cyclohexyloxycarbonyl-pyrrolo[1,2-a]pyrimidine,200 mL of chloroform, 40 mL of ethanol instead of methanol, and 8.0 g(59.1 mmol) of N-chlorosuccinic acid imide were used.

The melting point was higher than 300° C. The result of $^1$H-NMR(CDCl$_3$, 300 MHz) analysis was δ 7.42 (d, 2H), 7.20(d, 2H), 5.83 (s, 1H), 2.68 (s, 3H), 1.23–1.35(m), 0.95–1.05(m), 0.80(s, 21H), 0.42–0.58 (m).

Example 6

[Synthesis of the exemplary compound C-17]

11.0 g (14.9 mmol, 70% yield) of 2-amino-3-(4-methylphenyl)sulfonylcarbamoyl-6-chloro-7-(4-chlorophenyl)-8-(2,6-di-t-butyl-4-methyl)cyclohexyloxycarbonyl-pyrrolo[1,2-a]pyrimidine was obtained by carrying out the same procedure as that in Example 1, except that 15 g (21.2 mmol) of 2-amino-3-(4-methylphenyl)sulfonylcarbamoyl-7-(4-chlorophenyl)-8-(2,6-di-t-butyl-4-methyl)cyclohexyloxycarbonyl-pyrrolo[1,2-a]pyrimidine instead of 2-amino-3-phenylaminosulfonylcarbamoyl-7-(4-chlorophenyl)-8-(2,6-di-t-butyl-4-methyl)cyclohexyloxycarbonyl-pyrrolo[1,2-a]pyrimidine, 100 mL of chloroform, 20 mL of methanol, and 3.1 g (23.3 mmol) of N-chlorosuccinic acid imide were used.

The melting point was 280 to 285° C. The result of $^1$H-NMR(CDCl$_3$, 300 MHz) analysis was δ 7.98 (s, 2H), 7.41 (d, 2H), 7.32 (d, 2H), 5.82 (s, 1H), 2.42 (s, 3H), 1.12–1.35 (m), 0.95–1.05 (m), 0.77 (s, 21H), 0.42–0.58 (m).

Example 7

[Synthesis of the exemplary compound C-5]

0.63 g (5.08 mmol) of 4-methylthiophenol was added to 5 mL of an N,N-dimethylacetamide solution containing 0.15 g (3.81 mmol) of sodium hydride and the mixture was stirred for 15 minutes at room temperature. Then, 2.00 g (2.54 mmol) of 2-amino-3-phenylaminosulfonylcarbamoyl-6-bromo-7-(4-chlorophenyl)-8-(2,6-di-t-butyl-4-methyl)cyclohexyloxycarbonyl-pyrrolo[1,2-a]pyrimidine was added to the mixture at room temperature. The mixture thus obtained was stirred at 70° C. for 3 hours. After that, the reaction solution thus obtained was poured into a cold dilute hydrochloric acid solution and the reaction product was extracted with ethyl acetate. The organic layer was washed twice with a saturated aqueous solution of sodium chloride, and thereafter dried by using magnesium sulfate. After removal by filtration of the magnesium sulfate, the organic layer was concentrated. Next, the organic layer was subjected to purification by column chromatography. In this way, 0.85 g (1.02 mmol, 40% yield) of 2-amino-3-phenylaminosulfonylcarbamoyl-6-(4-methylphenylthio)-7-(4-chlorophenyl)-8-(2,6-di-t-butyl-4-methyl)cyclohexyloxycarbonyl-pyrrolo[2-a]pyrimidine was obtained.

The melting point was 242 to 245° C. The result of $^1$H-NMR(CDCl$_3$, 300 MHz) analysis was δ 7.18–7.40 (m), 7.05–7.15 (m), 6.95 (d, 2H), 6.82 (d, 2H), 5.83 (s, 1H), 2.30 (s, 3H), 1.12–1.35 (m), 0.95–1.05 (m), 0.77 (s, 21H), 0.42–0.58 (m).

[Heat-sensitive recording material]

Example 8

<Preparation of a microcapsule solution A)

2.8 parts of a diazonium salt (exemplary compound (3)-11, maximum absorption wavelength: 370 nm) and 10 parts of tricresyl phosphate were added to and uniformly mixed with 19 parts of ethyl acetate. This solution was admixed uniformly with 7.6 parts of "Takenate D-110N" (manufactured by Takeda Chemical Industries, Ltd.) as a capsule wall forming material. In this way, solution I was obtained.

Next, 46 parts of a 8% by weight aqueous solution of phthalated gelatin, 17.5 parts of water, and 2 parts of a 10% aqueous solution of sodium dodecylbenzenesulfonate were added to the solution I. The resulting mixture was emulsified at 40° C. and 10,000 rpm for 10 minutes. 20 parts of water were added to the emulsion thus obtained, and the emulsion was homogenized. Then, as an encapsulating reaction, the emulsion was kept at 40° C. for 3 hours while being stirred. In this way a microcapsule solution A was obtained. The average diameter of the microcapsules were in the range of 0.7 to 0.8 μm.

<Preparation of a coupler emulsion B)

3.0 parts of the exemplary compound (C-2) as a coupler, 3.0 parts of the exemplary compound (B-1) as a base, 0.5 parts of tricresyl phosphate, and 0.24 parts of diethyl maleate were dissolved in 10.5 parts of ethyl acetate. In this way, solution II was obtained.

The solution II was added to a solution prepared by uniformly blending 49 parts of a 15% by weight aqueous solution of lime-treated gelatin, 9.5 parts of a 10% aqueous solution of sodium dodecylbenzenesulfonate, and 35 parts of water at 40° C. The resulting mixture was emulsified at 40° C. and 10,000 rpm for 10 minutes by using a homogenizer. The emulsion thus obtained was stirred at 40° C. for 2 hours to remove the ethyl acetate by evaporation. Then, water, of an amount making up for the total of the evaporated ethyl acetate and water, was added to the emulsion. In this way a coupler emulsion B was obtained.

<Preparation of a coating solution C for forming a heat sensitive recording layer>

A coating solution C for forming a heat-sensitive recording layer was obtained by uniformly blending 3.6 parts of the microcapsule solution A, 3.3 parts of water, and 9.5 parts of the coupler emulsion B.

<Preparation of a coating solution D for forming a protective layer>

A coating solution D for forming a protective layer was obtained by a process which includes blending 100 parts of a 6% aqueous solution of itaconic acid-modified polyvinyl alcohol ("KL-318" manufactured by Kuraray Co., Ltd.) and 10 parts of a 30% dispersion liquid of an epoxy-modified polyamide ("FL-71" manufactured by Toho Chemical Co., Ltd.), and then admixing the resulting solution uniformly with 15 parts of a 40% dispersion solution of zinc stearate ("Hydrine Z" manufactured by Chukyo Oil and Fats Co., Ltd.).

<Coating>

The coating solution C for forming a heat-sensitive recording layer was applied by means of a wired bar to the surface of a printing paper substrate which had been made by laminating polyethylene to woodfree paper, and the coating layer was dried at 50° C. The coating solution D for forming a protective layer was then applied to the surface of the recording layer in the same way and dried in the same way to obtain a desired heat-sensitive recording material. The solid content of the coating of the recording layer and the protective layer were 8.0 g/m$^2$ and 1.2 g/m$^2$, respectively.

[Color formation test]

Using a thermal head (model KST) manufactured by Kyocera Corp., thermal printing was performed by selecting the electric power and the pulse width for the thermal head so that the recording energy per unit area was 50 mJ/mm$^2$. The entire surface of the recording material carrying the image thus obtained was then irradiated with light from an ultraviolet lamp having a central wavelength of 365 nm and an output power of 40 W for 15 seconds. The densities of image area and background area of the sample thus obtained were measured by a Macbeth densitometer.

[Evaluation of color hue]

Reflective spectrum of the image area, whose color had been produced by using the thermal head (model KST) manufactured by Kyocera Corp., were measured by using a UV/VIS spectroscope. The results were standardized by taking the maximum absorbance as 1. Accordingly, the smaller the absorbance in a 400 to 475 nm wavelength region, the better cyan color hue with little yellowish tinge.

[Lightfastness test of image area]

The image area, whose color had been produced by using the thermal head (model KST) manufactured by Kyocera Corp., was irradiated with light at 32,000 lux continuously for 72 hours using a lightfastness tester which uses a fuorescent lamp. After the test, the density of the image area was measured. An image area, which exhibits a higher density after the irradiation with light, has better lightfastness.

[Image fixation test]

Thermal printing was performed by selecting the electric power and the pulse width for the thermal head so that the recording energy per unit area was 40 mJ/mm$^2$ using the thermal model manufactured by Kyocera Corp. The density of the background area before and after the thermal printing was measured. The smaller the density after the printing, the better is the image fixation.

Example 9

A heat-sensitive recording material was prepared and evaluated in the same way as in Example 8, except that the emulsion was obtained by using a coupler (C-3) in place of the coupler (C-2) which was used in Example 8.

Example 10

A heat-sensitive recording material was prepared and evaluated in the same way as in Example 8, except that the emulsion was obtained by using a coupler (C-13) in place of the coupler (c-2) which was used in Example 8.

Example 11

A heat-sensitive recording material was prepared and evaluated in the same way as in Example 8, except that the emulsion was obtained by using a coupler (C-17) in place of the coupler (C-2) which was used in Example 8.

Example 12

A heat-sensitive recording material was prepared and evaluated in the same way as in Example 8, except that the emulsion was obtained by using a coupler (C-35) in place of the coupler (C-2) which was used in Example 8.

Example 13

A heat-sensitive recording material was prepared and evaluated in the same way as in Example 8, except that 0.5 parts of a reducing agent (R-5) was added to the emulsion B.

Example 14

A heat-sensitive recording material was prepared and evaluated in the same way as in Example 8, except that the 0.5 parts of a reducing agent (R-6) was added to the emulsion B.

Example 15

A heat-sensitive recording material was prepared and evaluated in the same way as in Example 8, except that a base (B-7) was used in place of the base (B-1) which was used in Example 8.

Example 16

A heat-sensitive recording material was prepared and evaluated in the same way as in Example 8, except that the microcapsule solution was prepared by using an exemplary compound (3)-i (maximum absorption wavelength: 370 nm) in place of the diazonium salt (exemplary compound (3)-11) which was used in Example 8.

Comparative Example 1

A heat-sensitive recording material was prepared and evaluated in the same way as in Example 8, except that the emulsion was obtained by using the following compound in place of the coupler (C-2) which was used in Example 8.

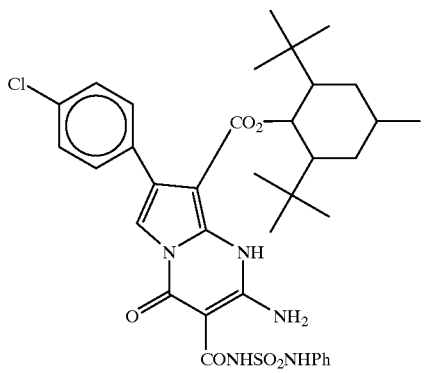

Comparative Example 2

A heat-sensitive recording material was prepared and evaluated in the same way as in Example 8, except that the emulsion was obtained by using the following compound in place of the coupler (C-2) which was used in Example 8.

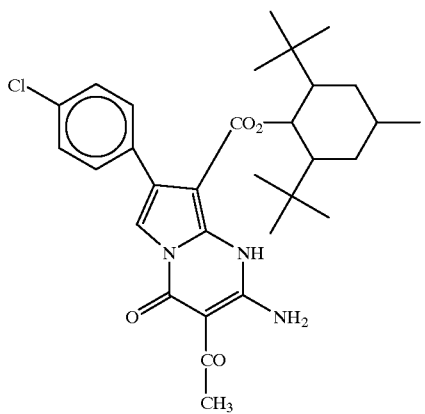

Comparative Example 3

A heat-sensitive recording material was prepared and evaluated in the same way as in Comparative Example 1, except that 0.5 parts of a reducing agent (R-6) was added to the emulsion B which was used in Comparative Example 1.

$\lambda_{max}$ of image area, and results of the image lightfastness test and the image fixation test are shown in Table 1.

TABLE 1

| Colored image | Image light-fastness density of image area | | Image fixation pro-perty density of background area | | |
|---|---|---|---|---|---|
| $\lambda_{max}$ (nm) | Before irradiation with light | After irradiation with light | Before printing | After printing | Color hue |
| Example 8 | 660 | 1.86 | 1.61 | 0.07 | 0.12 | Cyan |
| Example 9 | 661 | 1.80 | 1.55 | 0.07 | 0.13 | Cyan |
| Example 10 | 662 | 1.76 | 1.51 | 0.07 | 0.13 | Cyan |
| Example 11 | 659 | 1.78 | 1.55 | 0.06 | 0.11 | Cyan |
| Example 12 | 660 | 1.80 | 1.55 | 0.06 | 0.11 | Cyan |
| Example 13 | 661 | 1.95 | 1.78 | 0.07 | 0.11 | Cyan |
| Example 14 | 662 | 1.98 | 1.80 | 0.06 | 0.11 | Cyan |

TABLE 1-continued

| Colored image | Image light-fastness density of image area | | Image fixation pro-perty density of background area | | |
|---|---|---|---|---|---|
| $\lambda_{max}$ (nm) | Before irradiation with light | After irradiation with light | Before printing | After printing | Color hue |
| Example 15 | 660 | 2.01 | 1.81 | 0.06 | 0.10 | Cyan |
| Example 16 | 662 | 1.85 | 1.60 | 0.07 | 0.11 | Cyan |
| Comparative example 1 | 661 | 1.56 | 1.31 | 0.06 | 0.10 | Cyan |
| Comparative example 2 | 658 | 1.57 | 1.33 | 0.07 | 0.12 | Cyan |
| Comparative example 3 | 660 | 1.35 | 1.10 | 0.06 | 0.10 | Cyan |

From the results, it can be seen that the heat-sensitive recording materials using as couplers the pyrrolopyrimidineone compounds represented by the general formula (1) of the present invention produce higher color densities. Further, in these heat-sensitive recording materials, the absorption of yellow in image areas is smaller and the cyan color is better. Furthermore, in these heat-sensitive recording materials, the image lightfastness is better because the reduction of density in image area is slight even after the irradiation of light from a fluorescent lamp.

What is claimed is:

1. A pyrrolopyrimidineone compound represented by the following general formula (1):

wherein $R^1$ and $R^2$ each independently represents a hydrogen atom, a halogen atom, an aryl group, an alkyl group, a cyano group, an acyl group, a carbamoyl group, an alkoxycarbonyl group, an aryloxycarbonyl group, an alkylsulfonyl group, or an arylsulfonyl group; $R^3$ represents an amino group, a substituted amino group, a hydroxyl group, an acyloxy group, an arylcarboxyl group, an alkoxy group, an aryloxy group, an alkylthio group, or an arylthio group; $R^4$ represents a hydrogen atom, a halogen atom, or an electron attracting group whose Hammett substituent constant $\sigma_p$ is 0.2 or more; and L represents a substituent group which can leave when the compound reacts with a diazonium salt, wherein the pyrrolopyrimidineone compound is selected from the group consisting of the following compounds:

(C-1)

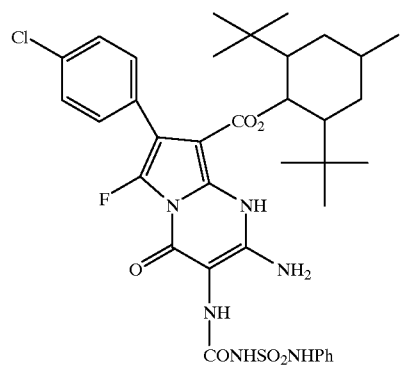

-continued (C-2)
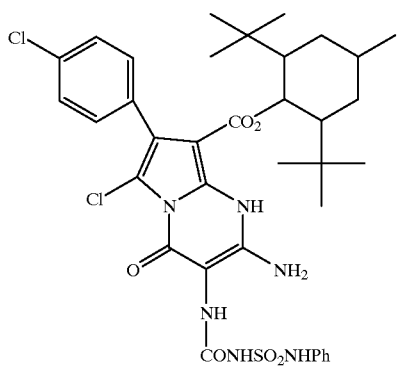

(C-3)
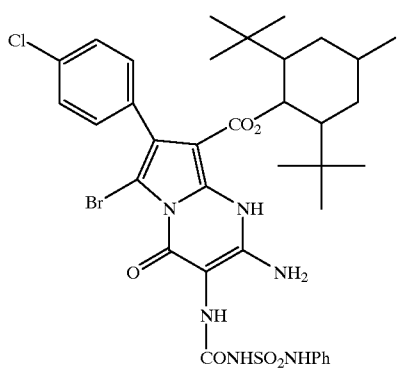

(C-4)
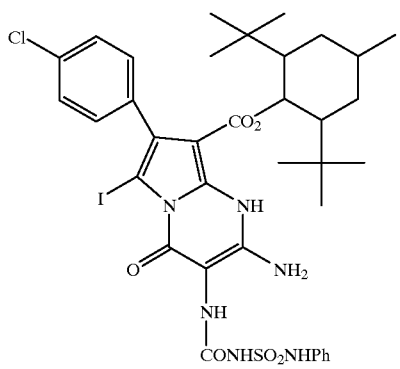

(C-5)
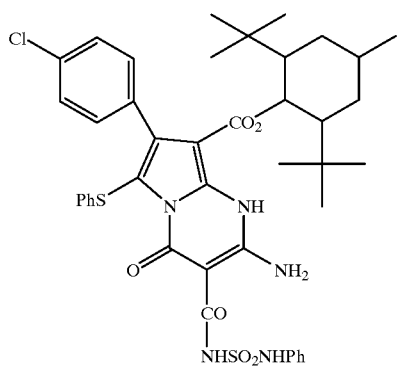

-continued (C-13)
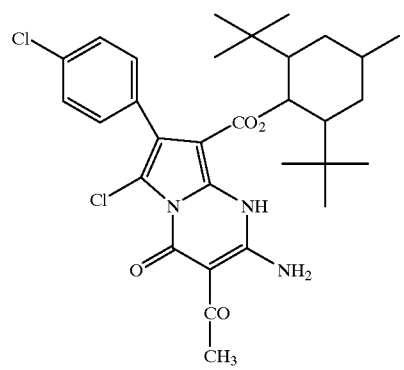

(C-17)
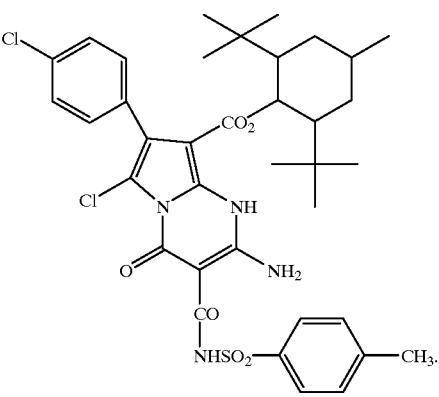

2. A heat-sensitive recording material comprising a substrate having thereon a heat-sensitive recording layer containing a diazonium salt and a coupler capable of forming a color by reacting with the diazonium salt when heated, wherein the coupler is a pyrrolopyrimidineone compound represented by the following general formula (1):

General formula (1)

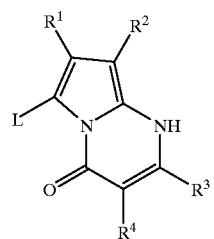

(1)

wherein $R^1$ and $R^2$ each independently represents a hydrogen atom, a halogen atom, an aryl group, an alkyl group, a cyano group, an acyl group, a carbamoyl group, an alkoxycarbonyl group, an aryloxycarbonyl group, an alkylsulfonyl group, or an arylsulfonyl group; $R^3$ represents an amino group, a substituted amino group, a hydroxyl group, an acyloxy group, an arylcarboxyl group, an alkoxy group, an aryloxy group, an alkylthio group, or an arylthio group; $R^4$ represents a hydrogen atom, a halogen atom, or an electron attracting group whose Hammett substituent constant $\sigma_p$ is 0.2 or more; and L represents a substituent group which can leave when the compound undergoes a reaction with a diazonium salt.

3. A heat-sensitive recording material according to claim 2, wherein the maximum absorption wavelength $\lambda_{max}$ of the diazonium salt is 450 nm or less.

4. A heat-sensitive recording material according to claim 2, wherein the diazonium salt is represented by any of the following formulae (2) to (4):

General formula (2)

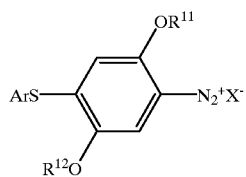

(2)

wherein Ar represents a substituted or unsubstituted aryl group; $R^{11}$ and $R^{12}$ each represents a substituted or unsubstituted alkyl group, or represents a substituted or unsubstituted aryl group, with the proviso that $R^{11}$ and $R^{12}$ may be the same or different; and $X^-$ represents an acid anion;

General formula (3)

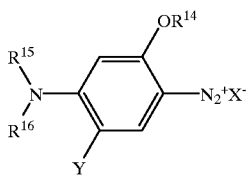

(3)

wherein $R^{14}$, $R^{15}$ and $R^{16}$ each represents a substituted or unsubstituted alkyl group, or represents a substituted or unsubstituted aryl group, with the proviso that $R^{14}$, $R^{15}$ and $R^{16}$ may be the same or different; Y represents a hydrogen atom or a —$OR^{13}$ group with the proviso that $R^{13}$ represents a substituted or unsubstituted alkyl group, or represents a substituted or unsubstituted aryl group; and $X^{31}$ represents an acid anion;

General formula (4)

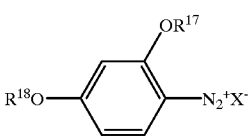

(4)

wherein $R^{17}$ and $R^{18}$ each represents a substituted or unsubstituted alkyl group, or represents a substituted or unsubstituted aryl group; and $X^{31}$ represents an acid anion.

5. A heat-sensitive recording material according to claim 3, wherein the diazonium salt is represented by any of the following formulae (2) to (4):

General formula (2)

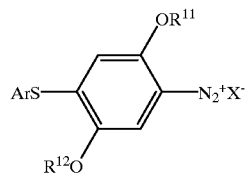

(2)

wherein Ar represents a substituted or unsubstituted aryl group; $R^{11}$ and $R^{12}$ each represents a substituted or unsubstituted alkyl group or represents a substituted or unsubstituted aryl group, with the proviso that $R^{11}$ and $R^{12}$ may be the same or different; and $X^-$ represents an acid anion;

General formula (3)

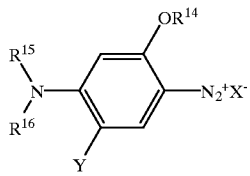

(3)

wherein $R^{14}$, $R^{15}$ and $R^{16}$ each represents a substituted or unsubstituted alkyl group or represents a substituted or unsubstituted aryl group, with the proviso that $R^{14}$, $R^{15}$ and $R^{16}$ may be the same or different; Y represents a hydrogen atom or a —$OR^{13}$ group with the proviso that $R^{13}$ represents a substituted or unsubstituted alkyl group, or represents a substituted or unsubstituted aryl group; and $X^-$ represents an acid anion;

General formula (4)

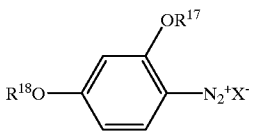

(4)

wherein $R^{17}$ and $R^{18}$ each represents a substituted or unsubstituted alkyl group or represents a substituted or unsubstituted aryl group; and $X^-$ represents an acid anion.

6. A heat-sensitive recording material according to claim 2, wherein the diazonium salt is enclosed in microcapsules.

7. A heat-sensitive recording material according to claim 6, wherein the capsule wall of the microcapsules comprises polyurethane and/or polyurea as a constituent component.

8. A heat-sensitive recording material according to claim 7, wherein the heat recording layer contains a reducing agent.

9. A heat-sensitive recording material according to claim 3, wherein the diazonium salt is enclosed in microcapsules.

10. A heat-sensitive recording material according to claim 9, wherein the capsule wall of the microcapsules comprises polyurethane and/or polyurea as a constituent component.

11. A heat-sensitive recording material according to claim 10, wherein the heat recording layer contains a reducing agent.

12. A heat-sensitive recording material according to claim 4, wherein the diazonium salt is enclosed in microcapsules.

13. A heat-sensitive recording material according to claim 12, wherein the capsule wall of the microcapsules comprises polyurethane and/or polyurea as a constituent component.

14. A heat-sensitive recording material according to claim 13, wherein the heat recording layer contains a reducing agent.

15. A heat-sensitive recording material according to claim 2, wherein the pyrrolopyrimidineone compound is selected from the group consisting of the following compounds:

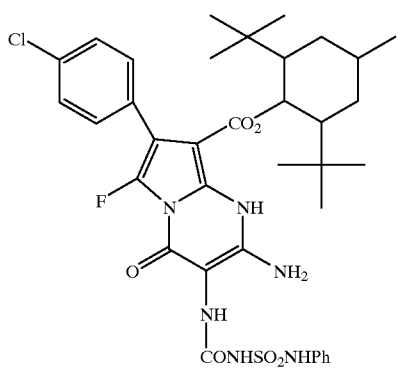
(C-1)

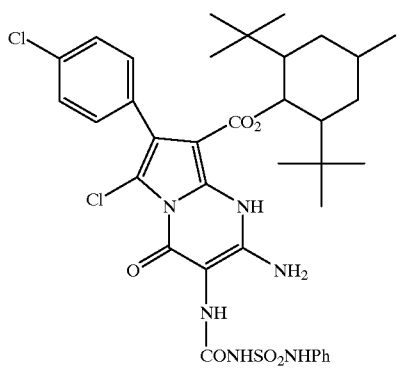
(C-2)

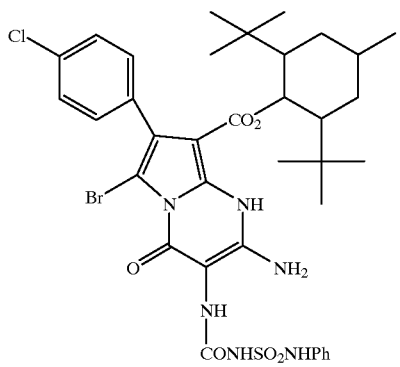
(C-3)

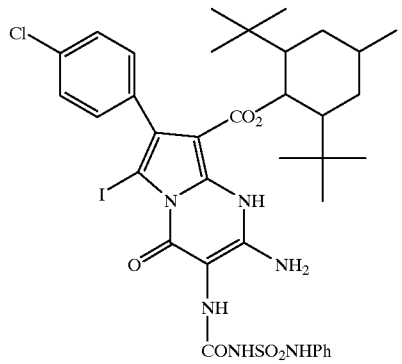
(C-4)

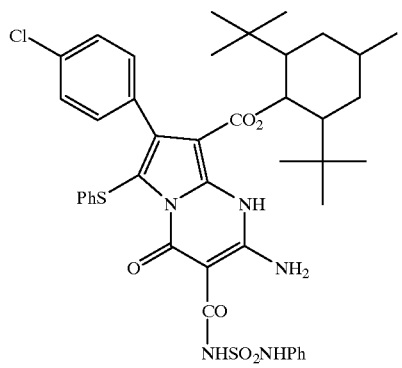
(C-5)

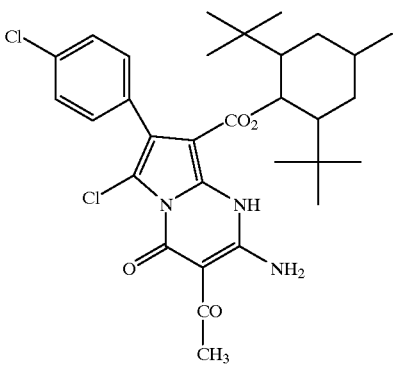
(C-13)

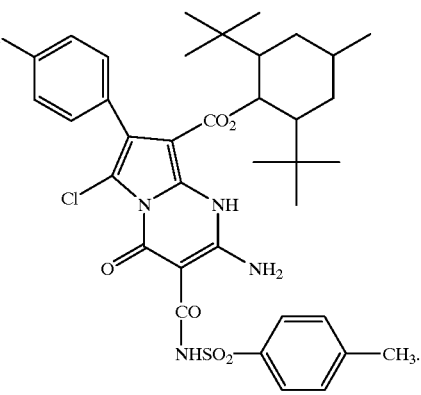
(C-17)

16. A heat-sensitive recording material according to claim 2, wherein the diazonium salt is selected from the group consisting of the following compounds:

(3)-1 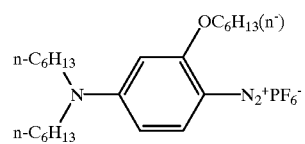
(3)-11 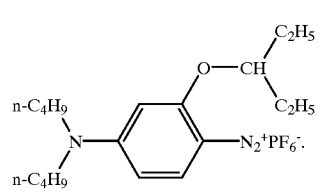
(3)-1 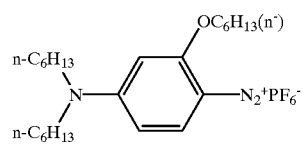
(3)-11 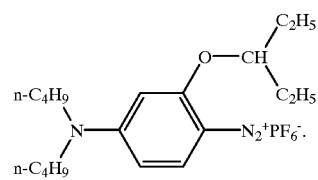
17. A heat-sensitive recording material according to claim 15, Wherein the diazonium salt is selected from the group consisting of the following compounds:
* * * * *